US010900962B2

(12) United States Patent
Stein et al.

(10) Patent No.: US 10,900,962 B2
(45) Date of Patent: *Jan. 26, 2021

(54) MOLECULAR NETS AND DEVICES FOR CAPTURING ANALYTES INCLUDING EXOSOMES

(71) Applicant: Sienna Cancer Diagnostics Inc., Minneapolis, MN (US)

(72) Inventors: Emily A. Stein, San Leandro, CA (US); Bruce Phelps, Clayton, CA (US); Robert Place, Bethesda, MD (US); Dina Uzri, San Diego, CA (US)

(73) Assignee: Sienna Cancer Diagnostics Inc., Minneapolis, MN (US)

( * ) Notice: Subject to any disclaimer, the term of this patent is extended or adjusted under 35 U.S.C. 154(b) by 268 days.

This patent is subject to a terminal disclaimer.

(21) Appl. No.: 15/642,393

(22) Filed: Jul. 6, 2017

(65) Prior Publication Data

US 2018/0143188 A1 May 24, 2018

Related U.S. Application Data

(63) Continuation of application No. 14/214,556, filed on Mar. 14, 2014, now Pat. No. 9,733,242, and a (Continued)

(51) Int. Cl.
*G01N 33/545* (2006.01)
*G01N 33/543* (2006.01)
(Continued)

(52) U.S. Cl.
CPC ..... *G01N 33/54353* (2013.01); *G01N 33/545* (2013.01); *G01N 33/54346* (2013.01);
(Continued)

(58) Field of Classification Search
CPC ....... G01N 33/54346; G01N 33/54353; G01N 33/545; G01N 33/569; G01N 33/56916;
(Continued)

(56) References Cited

U.S. PATENT DOCUMENTS 3,817,837 A 6/1974 Rubenstein et al.
3,850,752 A 11/1974 Schuurs et al.
(Continued)

FOREIGN PATENT DOCUMENTS

CN 1180260 C 12/2004
CN 1925871 A 3/2007
(Continued)

OTHER PUBLICATIONS

EP 10833970.6, Exam report dated Sep. 22. 2016, 9 pages.##.
(Continued)

*Primary Examiner* — Gailene Gabel
(74) *Attorney, Agent, or Firm* — ALGM LLP; Harry J. Guttman

(57) ABSTRACT

Disclosed is a covalently-linked multilayered three-dimensional matrix comprising capture molecules, linkers and spacers (referred to as a Molecular Net) for specific and sensitive analyte capture from a sample. Also disclosed herein is a Molecular Net comprising covalently-linked multilayered three-dimensional matrix comprising more than one type of capture molecule and more than one type of linker and may comprise one or more spacer for specific and sensitive capture of more than one type of analyte from a sample. A Molecular Net may comprise a pseudorandom nature. Use of various capture molecules, linkers and spacers in a Molecular Net may confer unique binding properties to a Molecular Net. Porosity, binding affinity, size exclusion abilities, filtration abilities, concentration abilities and signal amplification abilities of a Molecular Net may be varied and
(Continued)

depend on the nature of components used in its fabrication. Uses of a Molecular Net may include analyte capture, analyte enrichment, analyte purification, analyte detection, analyte measurement and analyte delivery. Molecular Nets may be used in liquid phase or on solid phases such as nanomaterials, modified metal surfaces, nanospheres, microspheres, microtiter plates, slides, pipettes, cassettes, cartridges, discs, probes, lateral flow devices, microfluidics devices, microfluidics devices, optical fibers and others.

41 Claims, 11 Drawing Sheets

Related U.S. Application Data continuation-in-part of application No. 13/938,055, filed on Jul. 9, 2013, now Pat. No. 9,910,040, said application No. 14/214,556 is a continuation-in-part of application No. 13/938,055, filed on Jul. 9, 2013, now Pat. No. 9,910,040, application No. 15/642,393, which is a continuation-in-part of application No. 13/511,364, filed on Oct. 7, 2012, now abandoned, said application No. 13/938,055 is a continuation-in-part of application No. 13/511,364, filed on Oct. 7, 2012, now abandoned, said application No. 14/214, 556 is a continuation of application No. 13/511,364, filed as application No. PCT/US2010/058086 on Nov. 24, 2010, now abandoned, which is a continuation of application No. 61/410,837, filed on Nov. 5, 2010.

(60) Provisional application No. 61/783,189, filed on Mar. 14, 2013, provisional application No. 61/669,261, filed on Jul. 9, 2012, provisional application No. 61/669,265, filed on Jul. 9, 2012, provisional application No. 61/343,467, filed on Apr. 29, 2010, provisional application No. 61/340,287, filed on Mar. 15, 2010, provisional application No. 61/337,257, filed on Feb. 1, 2010, provisional application No. 61/281,991, filed on Nov. 24, 2009.

(51) Int. Cl.
  *G01N 33/76* (2006.01)
  *G01N 33/569* (2006.01)
  *B01L 3/00* (2006.01)

(52) U.S. Cl.
  CPC ..... *G01N 33/54393* (2013.01); *G01N 33/569* (2013.01); *G01N 33/56916* (2013.01); *G01N 33/56938* (2013.01); *G01N 33/56983* (2013.01); *G01N 33/76* (2013.01); *B01L 3/502753* (2013.01); *G01N 33/56911* (2013.01); *G01N 2333/59* (2013.01)

(58) Field of Classification Search
  CPC ....... G01N 33/56938; G01N 33/56983; G01N 33/54393; G01N 33/76; G01N 33/56911; G01N 2333/59; B01L 3/502753
  See application file for complete search history.

(56) References Cited

U.S. PATENT DOCUMENTS

| 3,939,350 | A | 2/1976 | Kronick et al. |
|---|---|---|---|
| 3,996,345 | A | 12/1976 | Ullman et al. |
| 4,069,352 | A | 1/1978 | Parsons, Jr. |
| 4,232,119 | A | 11/1980 | Carlsson et al. |
| 4,275,149 | A | 6/1981 | Litman et al. |
| 4,277,437 | A | 7/1981 | Maggio |
| 4,366,241 | A | 12/1982 | Tom et al. |
| 4,434,150 | A | 2/1984 | Azad et al. |
| 4,511,478 | A | 4/1985 | Nowinski et al. |
| 4,590,169 | A | 5/1986 | Cragle et al. |
| 4,756,828 | A | 7/1988 | Litman et al. |
| 4,757,004 | A | 7/1988 | Houts et al. |
| 4,778,751 | A | 10/1988 | El Shami et al. |
| 4,829,101 | A | 5/1989 | Kraemer et al. |
| 4,879,215 | A | 11/1989 | Weng et al. |
| 4,883,688 | A | 11/1989 | Houts et al. |
| 4,945,205 | A | 7/1990 | Litman et al. |
| 4,960,691 | A | 10/1990 | Gordon et al. |
| 5,001,048 | A | 3/1991 | Taylor et al. |
| 5,585,481 | A | 12/1996 | Arnold et al. |
| 5,650,334 | A | 7/1997 | Zuk et al. |
| 5,876,830 | A | 3/1999 | Michl et al. |
| 5,914,230 | A | 6/1999 | Liu et al. |
| 5,994,089 | A | 11/1999 | Siiman et al. |
| 6,074,827 | A | 6/2000 | Nelson et al. |
| 6,627,460 | B1* | 9/2003 | Lihme .................. G01N 33/531 436/529 |
| 6,812,023 | B1* | 11/2004 | Lamparski ........... C12N 5/0639 435/325 |
| 7,612,168 | B2 | 11/2009 | Sorensen |
| 7,615,614 | B2 | 11/2009 | Hackett, Jr. et al. |
| 7,939,283 | B2 | 5/2011 | Chan et al. |
| 9,733,242 | B2* | 8/2017 | Stein ................ G01N 33/56938 |
| 2003/0003602 | A1 | 1/2003 | Vogt et al. |
| 2003/0116499 | A1 | 6/2003 | Ward et al. |
| 2003/0124623 | A1 | 7/2003 | Yager et al. |
| 2003/0149246 | A1 | 8/2003 | Russell |
| 2005/0037343 | A1 | 2/2005 | Fagnani et al. |
| 2005/0037413 | A1 | 2/2005 | Park et al. |
| 2005/0042612 | A1 | 2/2005 | Hubbard et al. |
| 2005/0112601 | A1 | 5/2005 | Hassibi et al. |
| 2006/0148096 | A1 | 7/2006 | Jina |
| 2006/0194197 | A1 | 8/2006 | Spangler et al. |
| 2006/0252074 | A1 | 11/2006 | Atzesberger et al. |
| 2007/0031283 | A1 | 2/2007 | Davis et al. |
| 2007/0117199 | A1* | 5/2007 | Nimri ............... G01N 33/54353 435/287.2 |
| 2007/0281366 | A1 | 12/2007 | Shimizu et al. |
| 2008/0145949 | A1 | 6/2008 | Song et al. |
| 2008/0280778 | A1 | 11/2008 | Urdea |
| 2009/0023144 | A1 | 1/2009 | Sun |
| 2009/0214762 | A1 | 8/2009 | Lewis et al. |
| 2013/0052653 | A1 | 2/2013 | Stein et al. |
| 2014/0080119 | A1 | 3/2014 | Stein et al. |
| 2014/0315759 | A1 | 10/2014 | Stein et al. |
| 2018/0023124 | A1* | 1/2018 | Collins ................ C12Q 1/6827 435/6.11 |

FOREIGN PATENT DOCUMENTS

| CN | 101514956 A | 8/2009 |
|---|---|---|
| CN | 101558301 B | 10/2009 |
| DE | 19703718 A1 | 7/1997 |
| EA | 200602280 A1 | 6/2007 |
| EP | 1577670 A2 | 9/2005 |
| EP | 2541250 A1 | 1/2013 |
| WO | 1989001335 A1 | 2/1989 |
| WO | 1993013121 A1 | 7/1993 |
| WO | 1995027902 A1 | 10/1995 |
| WO | 1995032305 A1 | 11/1995 |
| WO | 96/30409 A1 | 10/1996 |
| WO | 1997007398 A1 | 2/1997 |
| WO | 1999030145 A1 | 6/1999 |
| WO | 2000007019 A1 | 2/2000 |
| WO | 2001057533 A2 | 8/2001 |
| WO | 2003025573 A1 | 3/2003 |
| WO | 2005036171 A1 | 4/2005 |
| WO | 2005072479 A2 | 8/2005 |
| WO | 2005123952 A2 | 12/2005 |
| WO | 2007067189 A2 | 6/2007 |
| WO | 2008075216 A1 | 6/2008 |
| WO | 2009135388 A1 | 11/2009 |
| WO | 2011066449 A1 | 6/2011 |

(56) References Cited

FOREIGN PATENT DOCUMENTS

OTHER PUBLICATIONS

EP 13816747.3, Extended EP Search Report dated Nov. 2, 2016, 10 pages.##.
EP 14768268.6, Extended EP Search Report dated Jul. 21, 2016, 7 pages.##.
U.S. Appl. No. 13/511,364 Restriction Requirement dated Apr. 5, 2013, 5 pages.##.
U.S. Appl. No. 13/511,364 Response to Restriction Requirement filed Jun. 5, 2013, 5 pages.##.
U.S. Appl. No. 13/511,364 Advisory Action dated Nov. 18, 2014, 11 pages.##.
U.S. Appl. No. 13/511,364 RCE submission filed Jan. 26, 2015, 9 pages.##.
U.S. Appl. No. 13/511,364 Interview Summary dated Aug. 29, 2016, 4 pages.##.
U.S. Appl. No. 13/511,364 Statement of the Substance of the Interview filed Sep. 29, 2016, 4 pages.##.
U.S. Appl. No. 13/511,364 Final Office Action dated Dec. 30, 2016, 31 pages.##.
U.S. Appl. No. 13/938,055 Interview Summary dated Aug. 29, 2016, 4 pages.##.
U.S. Appl. No. 13/938,055 Statement of the Substance of the Interview filed Sep. 29, 2016, 4 pages.##.
U.S. Appl. No. 13/938,055 Final Office Action dated Dec. 1, 2016, 26 pages.##.
U.S. Appl. No. 13/938,055 RCE Response to Final Office Action filed Feb. 13, 2017, 13 pages.##.
Brynda et al., "The detection of human beta2-microglobulin by grating coupler immunosensor with three dimensional antibody networks" Biosensors & Bioelectronics (1999) vol. 14, pp. 363-368##.
CN 201480025377.0, First Office action dated Aug. 22, 2016, 17 pages.##.
CN 201480025377.0, First Office action dated Aug. 22, 2016, 17 pages of English translation.##.
U.S. Appl. No. 14/214,556 nonfinal Office Action dated Feb. 4, 2016, 14 pages.
U.S. Appl. No. 14/214,556 Response to nonfinal Office Action filed May 4, 2016, 17 pages.
U.S. Appl. No. 14/214,556 Supplemental Response filed Aug. 15, 2016, 17 pages.
U.S. Appl. No. 14/214,556 final Office Action dated Sep. 22, 2016, 23 pages.
U.S. Appl. No. 14/214,556 Response to final Office Action filed Dec. 21, 2016, 18 pages.
U.S. Appl. No. 14/214,556 Notice of Allowance and Allowability dated Mar. 27, 2017, 36 pages.
U.S. Appl. No. 14/214,556 Supplemental Notice of Allowability dated May 4, 2017, 2 pages.
U.S. Appl. No. 14/214,556 Rule 312 Amendment filed Jun. 15, 2017, 11 pages.
U.S. Appl. No. 14/214,556 Entry of Rule 312 Amendment dated Jun. 27, 2017, 8 pages.
CN 201080061738.9, Fourth Office action dated Jul. 4, 2016, 5 pages of English translation.##.
CN 201080061738.9, Fourth Office action dated Jul. 4, 2016, 6 pages.##.
CN 201080061738.9, Office action dated Jul. 2, 2014, 10 pages.##.
CN 201080061738.9, Office action dated Jul. 2, 2014, 7 pages of English-language summary.##.
CN 201080061738.9, Second Office action dated Apr. 24, 2015, 9 pages.##.
CN 201080061738.9, Second Office action dated Apr. 24, 2015, 9 pages of English translation.##.
CN 201080061738.9, Third Office action dated Dec. 23, 2015, 4 pages.##.
CN 201080061738.9, Third Office action dated Dec. 23, 2015, 5 pages of English translation.##.

English-language translation of Abstract from Thomson Innovation of Chinese Patent No. 101514956, 2 pages.##.
English-language translation of Abstract from Thomson Innovation of German Patent No. 19703718, 1 page.##.
EP 10833970.6, ESR dated Nov. 13, 2014, 9 pages.##.
EP 13816747.3, Partial Supplementary ESR dated Jul. 27, 2016, 8 pages.##.
PCT/US2010/058086, ISR/WO dated Feb. 28, 2011, 12 pages.##.
PCT/US2013/049779, ISR/WO dated Jan. 10, 2014, 20 pages.##.
PCT/US2014/029823, ISR/WO dated Aug. 28, 2014, 6 pages.##.
U.S. Appl. No. 13/511,364 Office Action dated Apr. 3, 2015, 15 pages.##.
U.S. Appl. No. 13/511,364 Office Action dated Feb. 11, 2016, 15 pages.##.
U.S. Appl. No. 13/511,364 Office Action dated Jul. 25, 2014, 7 pages.##.
U.S. Appl. No. 13/511,364 Office Action dated Sep. 25, 2013, 10 pages.##.
U.S. Appl. No. 13/511,364 Response filed Mar. 25, 2014, for Sep. 25, 2013, Office Action, 5 pages.##.
U.S. Appl. No. 13/511,364 Response filed Oct. 28, 2014, for Jul. 25, 2014, Office Action, 8 pages.##.
U.S. Appl. No. 13/511,364 Response filed Oct. 5, 2015, for Apr. 3, 2015, Office Action, 10 pages.##.
U.S. Appl. No. 13/511,364 Response filed Aug. 11, 2016, for Feb. 11, 2016, Office Action, 18 pages.##.
U.S. Appl. No. 13/938,055 Office Action dated Feb. 12, 2016, 19 pages.##.
U.S. Appl. No. 13/938,055 Response filed Aug. 11, 2016, for Feb. 12, 2016, Office Action, 21 pages.##.
Abrahams et al., "Assembly of porphyrin building blocks into network structures with large channels" Nature (1994) vol. 369, p. 727.##.
Abuknesha et al. (Abstract) "Labeling of biotin antibodies with horseradish peroxidase using cyanuric chloride." Nature Protocols, vol. 4, No. 4, pp. 452-460, Mar. 2009.##.
Brynda et al. "Antibody networks for surface plasmon resonance immunosensors" Sensors and Actuators B: Chemical, vol. 54, Nos. 1-2, pp. 132-136, Jan. 1999.##.
Chen et al., "Synthesis from DNA of a molecule with the connectivity of a cube" Nature (1991) vol. 350, No. 6319, pp. 631-633.##.
Cui et al., "Layer-by-layer assembly of multilayer films composed of avidin and biotin-labeled antibody for Immunosensing" Biosensors & Bioelectronics (2003) vol. 18, pp. 59-67.##.
Fagan et al., "Molecular engineering of solid-state materials: organometallic building blocks" J. Am. Chem. Soc. (1989) vol. 111, pp. 1698-1719.##.
Jothikumar et al. (Abstract) "Design of FRET-TaqMan probes for multiplex real-time PCR using an internal positive control" Biotechniques, vol. 46, No. 7, pp. 519-524, Jun. 2009.##.
Koubova et al. "Detection of foodborne pathogens using surface plasmon resonance biosensors" Sensors and Actuators B: Chemical, vol. 74, Nos. 1-3, pp. 100-105, Apr. 2001.##.
MacGillivray et al., "Interwoven two- and three-dimensional coordination polymers through self-assembly of CuI cations with linear bidentate ligands" J. Chem. Soc. Chem. Commun. (1994) vol. 11, pp. 1325-1326.##.
Ngundi et al., "Failure of layer-by-layer multilayers composed of neutravidin-biotin-labeled antibody for sandwich fluoroimmunosensing" Biosensors & Bioelectronics (2007) vol. 22, pp. 3243-3246.##.
Stein et al., "Turning Down the Heat: Design and Mechanism in Solid-State Synthesis" Science (1993) vol. 259, No. 5101, pp. 1558-1564.##.
Su et al. "Development of immunochips for the detection of dengue viral antigens" Analytica Chimica Acta, vol. 479, No. 2, pp. 117-123, Mar. 2003.##.
Taylor et al. "Quantitative and simultaneous detection of four bloodborne bacterial pathogens with a multi-channel SPR sensor" Biosensors and Bioelectronics, vol. 22, No. 5, pp. 752-758, Dec. 2006.##.
Van Ness et al., "A versatile solid support system for oligodeoxynucleotide probe-based hybridization assays" Nucleic Acids Research (1991a) vol. 19, No. 12, pp. 3345-3350.##.

(56) References Cited

OTHER PUBLICATIONS

Van Ness et al., "The use of oligodeoxynucletode probes in chaotrope-based hybridization solutions" Nucleic Acids Research (1991b) vol. 19, No. 19, pp. 5143-5151. ##.

Wang et al., "Molecular Tectonics. Three-Dimensional Organic Networks with Zeolite Properties" Am. Chem. Soc. (1994) vol. 116, p. 12119.##.

Yaghi et al., "Hydrothermal Synthesis of a Metal-Organic Framework Containing Large Rectangular Channels" J. Am. Chem. Soc. (1995) vol. 117, No. 41, p. 10401-10402.##.

Yamaguchi et al., "Preparation and properties of antibody polymers" Reactive and Functional Polymers (1998) vol. 37, pp. 245-250.##.

Zhang et al., "Geometrically-Controlled and Site-Specifically-Functionalized Phenylacetylene Macrocycles" J. Am. Chem. Soc. (1994) vol. 116, p. 4227-4239. ##.

\* cited by examiner

MOLECULAR NETS AND DEVICES FOR CAPTURING ANALYTES INCLUDING EXOSOMES

CROSS-REFERENCE TO RELATED APPLICATIONS

This application is a continuation of U.S. application Ser. No. 14/214,556 filed on Mar. 14, 2014 (which is herein incorporated by reference in its entirety), which claims the benefit U.S. Provisional Application No. 61/783,189, filed on Mar. 14, 2013 (which is herein incorporated by reference in its entirety).

This application is also a continuation-in-part of U.S. application Ser. No. 13/938,055 filed on Jul. 9, 2013 (which is herein incorporated by reference in its entirety), which claims the benefit of U.S. Provisional Application No. 61/699,261, filed on Jul. 9, 2012 (which is herein incorporated by reference in its entirety) and which claims the benefit of U.S. Provisional Application No. 61/669,265, filed on Jul. 9, 2012 (which is herein incorporated by reference in its entirety).

This application is also a continuation-in-part of U.S. application Ser. No. 13/511,364 with a 371(c) date of Oct. 7, 2012 (which is herein incorporated by reference in its entirety) which is a 371 national stage entry application of PCT/US10/58086 filed on Nov. 24, 2010 (which is herein incorporated by reference in its entirety), which (a) claims the benefit of U.S. Provisional Application No. 61/410,837, filed on Nov. 5, 2010 (which is herein incorporated by reference in its entirety), (b) claims the benefit of U.S. Provisional Application No. 61/343,467, filed on Apr. 29, 2010 (which is herein incorporated by reference in its entirety), (c) claims the benefit of U.S. Provisional Application No. 61/340,287, filed on Mar. 15, 2010 (which is herein incorporated by reference in its entirety), (d) claims the benefit of U.S. Provisional Application No. 61/337,257, filed on Feb. 1, 2010 (which is herein incorporated by reference in its entirety), and (e) claims the benefit of U.S. Provisional Application No. 61/281,991, filed on Nov. 24, 2009 (which is herein incorporated by reference in its entirety).

BACKGROUND

Current strategies for solid phase analyte capture, analyte detection and analyte measurement exist using a single layer of capture molecules absorbed or covalently tethered to a surface for direct real-time sensing or are used in conjunction with secondary detection steps in an indirect detection modality are well known in the art. Both direct and indirect methods have demonstrated limitations in sensitivity, specificity, signal-to-noise ratio and/or cost.

There is need for analyte capture technology for solid phase surfaces or devices that can selectively capture analytes from a complex sample with little or no sample preparation and to position said selected analytes in a manner to maximize captured analyte measurement and/or detection in a manner that is compatible with most technologies.

SUMMARY

Devices for capturing an analyte are described. In one embodiment, a device may comprise a solid phase and a molecular net coupled to at least a portion of a surface of the solid phase. The molecular net may include capture molecules of at least one type coupled to each other by linker molecules of a plurality of types to form a covalently-linked multi-layered three-dimensional matrix. The capture molecules may be configured to bind to the analyte.

Methods of manufacturing a device for capturing an analyte are also described. In one embodiment, a method may comprise providing a solid phase, and placing a molecular net on at least a portion of a surface of the solid phase. The molecular net may include capture molecules of at least one type coupled to each other by linker molecules of a plurality of types to form a covalently-linked multi-layered three-dimensional matrix. The capture molecules may be configured to bind to the analyte.

Methods of measuring a quantity of an analyte in a sample are also described. In one embodiment, a method may comprise providing one or more devices each comprising a solid phase and a molecular net covering at least a portion of a surface of the solid phase. The molecular net may include capture molecules of at least one type coupled to each other by linker molecules of a plurality of types to form a covalently-linked multi-layered three-dimensional matrix. The capture molecules configured to bind to the analyte. The method also comprises exposing the devices to the sample and allowing at least a portion of the analyte to bind to the capture molecules of the molecular nets of the devices.

DESCRIPTION

Figure 1:
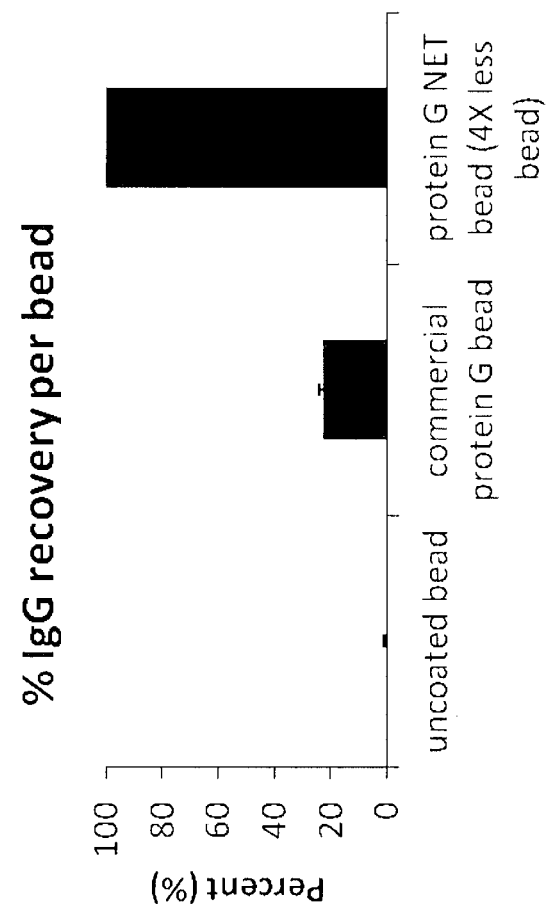
FIG. 1 shows a comparison of traditionally conjugated microparticles and Molecular Net microparticles in IgG purification.

It has been shown in U.S. patent Ser. Nos. 61/281,991, 61/337,257, 61/340,287, 61/343,467, 61/410,837, 61/489, 646, and 61/489,648, each of which are hereby incorporated by reference, that the construction and use of a covalently-linked pseudorandom multilayered three-dimensional matrix enables the rapid and specific capture of protein, nucleic acid, carbohydrate, lipid, cell or other analytes from an unprocessed sample and that the use of such Molecular Net may be a significant improvement upon conventional analyte binding approaches.

Design and Fabrication of Molecular Nets

Properties of Molecular Nets may be imparted by: the capture molecules selected for use (examples of capture molecules may include antibodies, nucleic acid probes, enzymes, recombinant proteins, peptides and others); the resultant specificity said capture molecules impart; the size and number of selected capture molecules; the placement and spacing of the capture molecules in the molecular Net layer(s); the combination of capture molecules; the order in which the capture molecules may be used; and the ratio of capture molecules to linker molecules and spacer molecules used.

Properties of Molecular Nets may also be imparted by: the linker molecules selected for use (examples of linker molecules include homobifunctional, heterobifunctional, trifunctional and multifunctional types); the chemical specificity of the linker molecules; the Angstrom length of the linker molecules; the combination of linker molecules; the order in which the linker molecules may be used; and the ratio of capture molecules to linker molecules and spacer molecules used.

Properties of Molecular Nets may also be imparted by: the spacer molecules selected for use (examples of spacer molecules include PEG, polymer, nucleic acid, albumin, Fc region, peptide, and other); the chemical properties of the spacer molecules; the size and number of spacer molecules; the order in which the spacer molecules may be used; and the ratio of spacer molecules to linker molecules and capture molecules used.

Placement and spacing of the capture molecules, linker molecules and spacer molecules may: confer a characteristic topology on the Molecular Net surface; confer a characteristic density within each layer of a Molecular Net; confer a characteristic porosity of a Molecular Net; remove spatial constraints and thus stearic hindrance; improve binding capacity; reduce non-specific binding; enable the binding of multiple forms of analyte (for example, simultaneous capture of degraded analyte, whole analyte and complexed analyte), and other.

The porosity within a Molecular Net may be random, pseudorandom or irregularly interspersed. Porosity of a Molecular Net may be used to filter a sample; may be used to discriminate binding potential molecules in a sample by size-exclusion; may be used to enable macromolecular or cellular binding due to the reduction in stearic hindrance, or other. The pores of a Molecular Net comprise capture molecules, linker molecules and may comprise spacer molecules. Traditional approaches to generate porosity on a solid phase relates to the mechanical modification of the surface of the solid phase and employ methods such as laser etching, laminating, lithography, laser printing or others to generate pores, holes or other structures in the solid surface. This solid surface is then prepared for accepting conjugating capture molecules. Use of a Molecular Net removes the need for mechanical modification of a surface and is thus more cost-effective. Additionally, traditional approaches are still hampered by the problem of high non-specific binding and require capture chemistry to be bound to the mechanically modified solid phase, which is not an improvement. Additionally, flexibility may be imparted into a Molecular Net as compared to the traditional capture format due to size-exclusion properties conferred by the porosity built into each layer of a Molecular Net. In some layers, pore diameter and depth may be similar or may vary depending on the application. In some layers, pore sizes may vary, the variance of which may depend on the application.

Porosity that may be imparted on a Molecular Net may include but are not limited to picopores, nanopores, micropores, filtration pores, sieving pores, pockets or other. Porosity may be imparted into a Molecular Net by the selection of and method of incorporation of specific capture molecules, linker molecules and spacer molecules into each layer of a Molecular Net. Porosity may also be imparted into a Molecular Net by the selection of and method of incorporation of specific capture molecules, linker molecules and spacer molecules used in the fabrication of sequential layers.

Molecular Net porosity may range from about 6 Angstroms in diameter to more than about 1 um in diameter based on the identity of capture molecules, linker and spacers used in a layer. In some cases, the porosity of a Molecular Net may comprise a range of pore diameters. Exemplary diameter ranges may be from about 5 nm to about 50 nm, from about 10 nm to about 100 nm, from about 50 nm to about 200 nm, from about 250 nm to about 500 nm, from about 500 nm to about 1 um, and from about 800 nm to about 1.5 um.

In some cases, capture molecules may be used to generate pores in a Molecular Net. In these instances, capture molecules may be pre-linked to one another prior to being incorporated into a Molecular Net layer. In some cases, linkers may be selected based on Angstrom length of the spacer arms. In some examples, extenders may be used to connect a first linker to a second linker to generate a long multi-functional linker. In some cases, spacers may be used to generate pores in a Molecular Net. Spacers may also be pre-linked to one another prior to being incorporated into a Molecular Net layer. In other examples, inert physical plugs may be used to build a pore, whereby each physical plug may be placed on a previously built layer while a new layer is being constructed. After curing, the physical plugs may be removed, thus leaving a pore of a specific diameter.

The flexible nature of the Molecular Net enables the use of multiple types of capture molecules. In some examples, a Molecular Net comprises a single type of capture molecule. In other examples, a Molecular Net comprises multiple types of capture molecules. In some examples, the use of more than one monoclonal antibody during the fabrication of a Molecular Net enables said Molecular Net to bind more than one epitope of an analyte. Use of more than one type of epitope-specific capture molecule enables improved analyte capture by a Molecular Net and relates to its performance. In some examples, the use of more than one nucleic acid sequence may be used during the fabrication process to generate a Molecular Net capable of binding to more than one epitope of an analyte. Examples of benefit depend on the use of the Molecular Net and may comprise improved performance in terms of minimum levels of detection, sensitivity, positive predictive value, negative predictive value, ability to work with degraded samples, ability to work with a diverse population, and others when used in a test; may comprise improved performance in binding capacity, purity, binding kinetics, target analyte depletion, and others when used as a purification tool; or other.

In some examples, the use of capture molecules directed against mutually-confirmatory analytes may be used in a Molecular Net and relates to its performance. Use of mutually-confirmatory capture molecules in a Molecular Net may be used in a confirmatory manner, whereby the capture of more than one analyte may provide a more statistically significant positive result; may provide a more robust test result; may provide additional information regarding a sample; and other. Use of mutually-confirmatory capture molecules in a Molecular Net may also be used to qualify a sample or may be used as a control in a test or may be used to measure more than one related molecular variable linked to a disease state or may be used to measure more than one related molecular variable linked to the treatment of a disease.

Examples of mutually-confirmatory analytes a Molecular Net may be fabricated to simultaneously capture from a sample may include: genetic sequence and corresponding protein product (for examples, cancer-related SNPs in BRCA1 and BRCA1 protein); the mRNA and corresponding protein product (for example, human lactase mRNA and Lactase protein); the genetic sequence and the corresponding mRNA product (for example, disease-related SNPs in LMNA and pre-spliced or spliced Lamin A/C mRNA); miRNA and related mRNA or protein products (miR 9 and REST or CoREST mRNA, or miR 9 and REST protein); small molecule drugs and drug targets (tofacitinib and Janus kinase 3); epitope-specific biologics and the respective targets (for example, anti-TNF antibodies and circulating TNF cytokine); epitope-specific antibodies, epitope-specific T cells and/or epitope-specific B cells or the like (for example, anti-DNA autoantibodies, anti-DNA CD4$^+$ T cells and/or anti-DNA B cells); or others. Examples of benefit depend on use and may relate to improved performance in test sensitivity, positive predictive value, negative predictive value, specificity, diagnosis of a disease, ability to work with samples experiencing genetic drift, ability to measure response to a therapeutic, ability to measure effectiveness of a therapeutic, or other.

In one example, a Molecular Net may be fabricated in a manner to capture and position bound analytes in a manner that enhances the intensity of a detectable signal or may enhance detection of bound analytes, such as when used in a test with optical detection. Placement of captured analytes in a layered manner by pre-positioned layered capture molecules may enable the rapid detection of analyte by signal intensification. Examples of signal intensification by a Molecular Net may relate to fluorescence, fluorescence resonance energy transfer, absorbance, luminescence, light scatter, surface plasmon resonance, optical heterodyne detection, or other.

Said Molecular Net may be designed and fabricated to replace the need for costly and time-intensive methods for ultra-sensitive detection such as PCR, branched DNA, or multi-step detection methods required for signal amplification. Said Molecular Net may also be designed and fabricated to replace the need for costly and complicated analytical devices.

Generally, the number of capture molecules incorporated into a 3-dimensional Molecular Net matrix is less than or equivalent to the number of capture molecules conjugated in a 2-dimensional manner to a surface using conventional approaches. Two-dimensional capture molecule-surface conjugates may rely on the use of a single linker type or may rely on the sequential use of 2 linkers to conjugate capture molecules to a solid surface. During the fabrication of a layer of a Molecular Net, multiple linker types are used simultaneously to link capture molecule to capture molecule of a new layer and the linked capture molecules of a new layer to a spacer or capture molecule of a previous layer. Molecular Nets may be fabricated in solution prior to placement on a solid surface. Pre-fabricated Molecular Nets may be absorbed or covalently linked to a solid surface. Molecular Nets may also be fabricated directly onto a solid surface, layer by layer. Said Molecular Nets may be placed on a solid surface using non-covalent (electrostatic, van der Waals, or other) or covalent methods. In some instances, polystyrene, polyurethane, polyethylene or treated surfaces such as poly-L-lysine coated surfaces, modified surfaces comprising —COOH, NHS, amine or other may be purchased from commercial sources (examples of vendors may include Thermo, Millipore, Luminex and other) and used as solid phase surfaces for Molecular Net placement. In other instances, solid phase surfaces may be pre-treated by chemicals such as acid to activate the surface moieties and thus to generate attachment points between the solid phase surface and reactive moieties of a Molecular Net. In some examples, a solid phase may be pre-treated with linker to covalently link a solid phase surface to a Molecular Net.

Design and fabrication of a Molecular Net for use on a solid phase surface may result in a covalently-linked multilayered three-dimensional matrix of capture molecules secured by covalent connectors within each layer. Design and fabrication may occur in a sequential manner where a first layer is fabricated and subsequent layers are fabricated in a sequential manner whereby each layer may be interconnected in a covalent manner to enhance structural integrity, topology, porosity and/or stability. Selection of individual capture molecules, linkers and spacers may be made to contribute to one or more property of a Molecular Net. Properties may comprise analyte specificity, thermal stability, layer thickness, pore diameter, absorbance spectra, emission spectra, solid phase compatibility or other.

The use of capture molecules and linker molecules and spacers of known lengths and widths may be used to generate various topology on the surface of the Molecular Net. Topological features that may be imparted on a Molecular Net may include but are not limited to dimples, pocks, stipples, pores, mounds, branches, filaments, fibers, fissures, raised segments or other and may be arranged in a Molecular Net in a random, pseudorandom or irregular manner.

Topological features of a Molecular Net may be generated through the use of capture molecules and linkers; capture molecules, linkers and spacers; or linkers and spacers. In some cases, capture molecules may be used to generate topological features of a Molecular Net. In these instances, capture molecules may be pre-linked to one another prior to being incorporated covalently into a Molecular Net layer. In some cases, linkers may be selected based on Angstrom length of the spacer arms. In some examples, spacers may be used to connect a first linker to a second linker to generate a long multi-functional linker. In some cases, spacers may be used to generate topological in a Molecular Net. Spacers may also be pre-linked to one another or to capture molecules prior to being incorporated into a Molecular Net layer.

Molecular nets may be designed and fabricated to impart characteristics such as affinity, size exclusion, filtration, fluorescence, and other into each layer of a Molecular Net. Specific capture molecules, linker molecules and spacer molecules may be selected based on size, length, diameter, thickness, optical properties, chemical properties or other for imparting characteristics into a Molecular Net during the fabrication process.

Molecular Nets may be fabricated in a manner whereby one or more capture molecules may serve a structural role, may serve both a structural role and a role in analyte capture within the covalently-linked multilayered three-dimensional matrix. Some examples of capture molecules that may be used for structural and/or analyte capture roles in a Molecular Net.

The distance between capture molecules in each layer of a Molecular Net may be determined, in part, by the diameter, width and/or length of capture molecules, linkers and spacers used in the fabrication process for each layer, whereby the molar relationship between each linker-capture-spacer molecule may be similar or may be different and the selection of said molecules may be dependent on size and/or shape of the analyte to be captured, the method used to measure captured analyte and/or desired use.

Molecular Nets may be designed and fabricated in a manner whereby each capture molecule, linker and spacer component may have equivalent or non-equivalent molar ratios in a layer of said Molecular Net. Variance of molar ratios between said components may be used from time to time to generate porosities or other topological features within each layer. Said porosities and topological features may have a range of diameters and may have a range of associated depths. Variance of molar ratios between Molecular Net components may occur in a single layer of Molecular Net or may occur in more than one layer of a Molecular Net and is dependent on the intended use of a Molecular Net.

TABLE 1

Examples of Molecular Net structural components with analyte capture ability.

| Examples of Molecular Net Structural/Capture Components | Approximate Diameter (nm) | Approximate Length (nm) |
|---|---|---|
| IgG, IgE | ~9 | 16 |
| IgM | 37 | 37 |
| IgA | ~9 | ~32 |
| Streptavidin & recombinant variants | ~105 (tetrameric) | N/A |
| Protein A & recombinant variants | ~3.2-5.3 | N/A |
| Protein G & recombinant variants | ~3-5.4 | N/A |
| MHC I | 3.05 | N/A |
| MHC II | 2.99 | N/A |
| TCR | 3.34 | N/A |
| CD28 | 2.75 | N/A |
| TLR 4 | 2.62 | N/A |
| B7x | 4.52 | N/A |
| Taq polymerase | ~6.49 | N/A |
| poly($Arg_9$) peptide | 1.43 | N/A |
| HSP70 | 3.46 | N/A |

Some examples of analyte dimensions that may be considered during the design and fabrication process are provided in Table 2. Design and fabrication of Molecular Net surface chemistry, pore diameter, topology, layering or other may be based on analyte shape; analyte structure, analyte isoforms, analyte charge, analyte complex formation with other molecules, and other forms. Furthermore, Molecular Nets may be designed and fabricated to bind and capture said analyte or may be designed and fabricated to exclude said analyte. Examples of analytes and analyte sizes can be found in Table 2.

TABLE 2

Examples of analytes and their dimensions.

| Exemplary Analyte | Approximate Diameter (um) | Approximate Length (um) |
|---|---|---|
| *E. coli* | 0.5 | 1-2 |
| *Klebsiella* spp. | 0.3-1 | 0.6-6 |
| *Pseudomonas* spp. | 0.6 | 3 |
| *Staphylococcus aureus* | 1 | 1 |
| *Staphylococcus aureus* (cluster) | >10 | >10 |
| Enterotoxin K | ~4.29 | N/A |
| Peptidoglycan, gram negative bacteria | ~2-3, species dependent | Highly species dependent |
| Outer membrane, gram negative bacteria | ~7, species dependent | Species dependent |
| IgG, IgE | 0.009 | 0.016 |
| IgA | 0.009 | 0.032 |
| IgM | 0.037 | 0.037 |
| B cell - G0 phase of cell cycle | 4.5-5.5 | N/A |
| B cell - early G1 phase of cell cycle | 5.5-7 | N/A |
| B cell - late G1 and S phase of cell cycle | 7-10 | N/A |
| B cell - late S, G2 and M phases of cell cycle | 10-12 | N/A |
| Monocyte | ~9-18 | N/A |
| Macrophage | 21, activation level dependent | N/A |
| Neutrophil | 7.17-9.3, activation level dependent | N/A |
| IL6 monomer | ~4.11 | N/A |
| IL6 multimer (variable) | ~6.16 | N/A |
| IL10 monomer | ~3.88 | N/A |
| IL10 multimer (variable) | ~7.7 | N/A |
| microRNA-146a | ~3-6 | ~7-9 |

Molecular Nets comprising structural components and capture components may be arranged in the covalently linked 3-dimensional (3D) multilayered matrix and may relate to the capture of one or more analyte relating to one or more of the following characteristics: surface chemistry; analyte shape; analyte structure; analyte isoforms; analyte charge; post-translational modification; chemical modification; activity; or other.

Molecular Nets may comprise structural components that also act in a manner relating to the capture of analytes and may be arranged in the interconnected 3D multilayered matrix of a Molecular Net by covalent linkers. A Molecular Net may also comprise spacers to interconnect said structure/capture molecules in a manner to maximize structural reinforcement, stability and/or specific analyte capture capability. Molecular Net examples comprising capture components/structural components, linkers and spacers are presented in Table 3.

Fabrication of the molecular Net is unique in that capture molecules are secured in a 3D matrix by covalent linker molecules. In numerous studies, Molecular Nets have been demonstrated to have improved thermal stability and extend shelf-life beyond traditional capture technologies.

TABLE 3

Examples of Molecular Nets and their Use.

| Analyte to Capture | Capture Molecules to Use for Affinity Capture | Methods of Generating Size Exclusion | Anticipated Use |
|---|---|---|---|
| *E. coli* | Antibodies against surface antigens (e.g., LPS, O-antigen, pili, | Covalently linked antibodies - IgG, IgM, covalent | Diagnostics: Food safety, infectious disease, water safety; |

TABLE 3-continued

Examples of Molecular Nets and their Use.

| Analyte to Capture | Capture Molecules to Use for Affinity Capture | Methods of Generating Size Exclusion | Anticipated Use |
|---|---|---|---|
| | other); PNA probes against chromosomal and/or plasmid DNA | linkers, spacers | Molecular tools: polymicrobial sampling, microbiome sampling, molecular biology |
| Klebsiella spp. | Antibodies against surface antigens (e.g., LPS, other); PNA probes against chromosomal and/or plasmid DNA | Covalently linked antibodies - IgG, IgM, covalent linkers, spacers | Diagnostics: Food safety, infectious disease, water safety; Molecular tools: polymicrobial sampling, microbiome sampling, molecular biology |
| Pseudomonas spp. | Antibodies against surface antigens (e.g., LPS, V antigen, other), excreted materials (e.g., heat shock proteins, alginate, other); PNA probes against chromosomal and/or plasmid DNA | Covalently linked antibodies - IgG, IgM, covalent linkers, spacers | Diagnostics: Food safety, infectious disease, water safety; Molecular tools: polymicrobial sampling, microbiome sampling, molecular biology |
| Staphylococcus aureus | Antibodies against surface antigens (e.g., protein A, peptidoglycan, other), excreted materials (e.g., heat shock proteins, exotoxins, other); PNA probes against chromosomal and/or plasmid DNA | Covalently linked antibodies - IgG, IgM, covalent linkers, spacers | Diagnostics: Food safety, infectious disease, water safety; Molecular tools: polymicrobial sampling, microbiome sampling, molecular biology |
| Staphylococcus aureus (cluster) | Antibodies against surface antigens (e.g., protein A, peptidoglycan, other), excreted materials (e.g., heat shock proteins, exotoxins, other); PNA probes against chromosomal and/or plasmid DNA | Covalently linked antibodies - IgG, IgM, covalent linkers, longer spacers | Diagnostics: Food safety, infectious disease, water safety; Molecular tools: polymicrobial sampling, microbiome sampling, molecular biology |
| IgG, IgE | Antibodies against Fc IgG or IgE; Antibodies against Fab; antigens | Covalently linked antibodies, antigens, covalent linkers, spacers | Diagnostics: Immune response profiling, vaccination, antibody titering; Molecular tools: immunologic studies, pre-clinical studies |
| IgA | Antibodies against Fc IgA; Antibodies against Fab IgA; antigens | Covalently linked antibodies, antigens, covalent linkers, spacers | Diagnostics: Immune response profiling, vaccination, antibody titering; Molecular tools: immunologic studies, pre-clinical studies |
| IgM | Antibodies against IgM; Antibodies against 5☐ IgM; antigens | Covalently linked antibodies, antigens, covalent linkers, spacers | Diagnostics: Immune response profiling, vaccination, antibody titering; Molecular tools: immunologic studies, pre-clinical studies |
| B cell - G0 phase of cell cycle | Antibodies against PAX5, CD19, CD20, CD79a, others; antigens; TCR: antigen; MHC I: antigen; MCH II: antigen; cytokines (e.g., IL10, IL6, TGFb, other) | Covalently linked antibodies - IgG, IgM, covalent linkers, spacers, MHC: antigen complexes, cytokines | Diagnostics: Immune response profiling, disease monitoring; Molecular tools: immunologic studies, pre-clinical studies |
| B cell - early G1 phase of cell cycle | Antibodies against PAX5, CD19, CD20, CD79a, others; | Covalently linked antibodies - IgG, IgM, covalent | Diagnostics: Immune response profiling, disease monitoring; |

TABLE 3-continued

Examples of Molecular Nets and their Use.

| Analyte to Capture | Capture Molecules to Use for Affinity Capture | Methods of Generating Size Exclusion | Anticipated Use |
|---|---|---|---|
| | antigens; TCR: antigen; MHC I: antigen; MCH II: antigen; cytokines (e.g., IL10, IL6, TGFb, other) | linkers, spacers, MHC: antigen complexes, cytokines | Molecular tools: immunologic studies, pre-clinical studies |
| B cell - late G1 and S phase of cell cycle | Antibodies against PAX5, CD19, CD20, CD79a, others; antigens; TCR: antigen; MHC I: antigen; MCH II: antigen; cytokines (e.g., IL10, IL6, TGFb, other) | Covalently linked antibodies - IgG, IgM, covalent linkers, spacers, MHC: antigen complexes, cytokines | Diagnostics: Immune response profiling, disease monitoring; Molecular tools: immunologic studies, pre-clinical studies |
| B cell - late S, G2 and M phases of cell cycle | Antibodies against PAX5, CD19, CD20, CD79a, others; antigens; TCR: antigen; MHC I: antigen; MCH II: antigen; cytokines (e.g., IL10, IL6, TGFb, other) | Covalently linked antibodies - IgG, IgM, covalent linkers, spacers, MHC: antigen complexes, cytokines | Diagnostics: Immune response profiling, disease monitoring; Molecular tools: immunologic studies, pre-clinical studies |
| Macrophage | Complement, antibodies against mannose receptor Ab, anti-Ly6C, or other; antibodies against M1, M2a, M2b, M2c markers; TLR agonists; cytokines; DAMPs; PAMPs; alarmins | Covalently linked antibodies - IgG, IgM, covalent linkers, spacers, MHC: antigen complexes, cytokines, TLR agonists, DAMPs, PAMPs, alarmins | Diagnostics: Immune response profiling, infectious disease monitoring; vaccination monitoring; chronic inflammatory disease monitoring; Molecular tools: immunologic studies, pre-clinical studies |
| Neutrophil | Complement, antibodies against CD15, Ly6G or other; antibodies against neutrophil markers; TLR agonists; cytokines; DAMPs; PAMPs; alarmins | Covalently linked antibodies - IgG, IgM, covalent linkers, spacers, MHC: antigen complexes, cytokines, TLR agonists, DAMPs, PAMPs, alarmins | Diagnostics: Immune response profiling, infectious disease monitoring; vaccination monitoring; chronic inflammatory disease monitoring; Molecular tools: immunologic studies, pre-clinical studies |
| Cytokines | Antibodies against one or more epitope of cytokine; cytokine binding domain of cytokine receptor; PNA probes against cytokine gene and/or cytokine mRNA; or other | Covalently linked antibodies - IgG, IgM, covalent linkers, spacers, | Diagnostics: Immune response profiling, infectious disease monitoring; vaccination monitoring; chronic inflammatory disease monitoring; Molecular tools: immunologic studies, pre-clinical studies |

In some examples, the solid phase may be particles ranging from about 2 nm in diameter to about 200 mm in diameter and Molecular Nets may be attached to the surface of said particle. Particles may comprise polystyrene, polyethylene, silica, composite, nylon, PVDF, nitrocellulose, cellulosic, carbon, or other may be magnetic, paramagnetic, fluorescent, barcoded or other.

Molecular Nets may be absorbed or covalently linked to the surface of a particle in manner to generate pseudorandom or ordered porosities in a single layer of said Molecular Net or throughout. In its most basic form, a particle may be initially coated with a layer of Molecular Net, which may be connected to a second layer, which may be connected to a third layer. Molecular Net layers may comprise the same capture molecules at the same or at different concentrations in each layer. Molecular Net particles may also comprise different capture molecules in each layer and may be fabricated in a manner to incorporate the same or different concentrations of capture molecules compared to previous layers.

In some examples, Molecular Nets may be attached to a particle surface in a manner to generate an asymmetric particle having a pre-determined polarity. Such a particle may be designed and fabricated with an initial layer comprising structural molecules with a large diameter, width and/or length and may be linked to a particle in an asymmetric manner to generate a polarity. A second layer may be linked to a first layer and a third layer may be connected to a second layer and so on. The number of layers in a Molecular Net particle may vary depending on use.

In some examples, Molecular Nets may be attached to a segment of a particle to generate an asymmetric particle having a pre-determined polarity. Such a particle is constructed whereby the initial layer is coated onto a segment of a particle and whereby a second layer is connected to the initial layer onto the same segment of said particle, and whereby a third layer is connected to the second layer onto the same segment of said particle, and whereby a fourth layer is connected to the third layer onto the same segment of said particle.

In some examples, Molecular Nets may be passively absorbed to a nonfunctionalized particle surface. In other examples, particle surfaces may be functionalized and may require activation prior to attachment. In other examples, particle surfaces may be activated prior to functionalization, at which time a Molecular Net may be attached. Yet in other examples, Molecular Nets may be constructed directly on the particle surface. Attachment of Molecular Nets to a particle may change the physical and/or chemical features of said particle. In some examples, Molecular Nets may comprise pseudorandom topological features placed on the surface of a particle. In some examples, Molecular Net particles may comprise topological features, the topological features comprising capture molecules and linkers and may also comprise spacers. Examples of various topological features may include appendages, spikes, plateaus, planes, mounds, fissures, pellicles, stipples, channels, pores and other and may be comprised of capture components directly linked within and/or linked to one or more layer of a Molecular Net.

Other examples of topological features may comprise be pockets, pillars, bumps, branches, projections, ridges, clefts, trellis-like structures, flakes, pellets, spheres, or others. Topological features may be pre-formed in solution and linked to the Molecular Net or may be formed at the time each layer is constructed.

Molecular Nets on particles may comprise heterogeneous capture molecules within one or more layer of a Molecular Net. Benefits of a heterogeneous design may relate to the capture of a plurality of analytes having a plurality of surface chemistries on a single particle. Heterogeneous capture molecules incorporated into a Molecular Net during fabrication may be randomly distributed throughout each layer; may be stratified throughout each layer; or other, depending on use.

Molecular Nets may be attached to particles to increase surface area of said particle. Molecular Nets may also be used to increase particle diameter. Topological features of a Molecular Net on a particle may relate to an increased particle size in addition to analyte capture capacity.

In some examples, a first layer of Molecular Net may be attached to a particle surface to modify the physical and/or chemical properties of particle. In many commercial particles, "bead effects" or "surface effects" can hamper results and are still not well understood. Traditional conjugation techniques that result in 2D conjugates and 2D conjugated surfaces often suffer from surface effects. Molecular Nets may be used to minimize or neutralize bead effects to minimize non-specific binding to a bead surface, bead autofluorescence, bead interference with in an assay or other. In some examples, Molecular Net particles may impart increased analyte binding capacity and may also impart blockade of non-specific binding of undesired analytes to increase the signal-to-noise ratio in an assay, yield and purity of purified analyte or other.

In some examples In yet another aspect, the invention features molecular Net on particle containing more than one layer, wherein each layer contains capture molecules directed against analyte, wherein each layer contains distinct capture molecules directed against distinct analyte, wherein different layers can be directed against different analytes to enable the capture of analyte or a plurality of analytes.

In yet another aspect, a Molecular Net placed on a solid phase surface may be used to increase the purity of one or more analyte recovered from a sample. Molecular Net-coated surfaces may reduce non-specific binding of undesired analyte compared to commercial 2D functionalized surfaces.

In some examples, Molecular Nets placed on particles may significantly increase analyte capture capacity of a particle. Additional layering of a Molecular Net may further increase the number of bound analyte per particle and may be used to enhance recovery or yield of analyte from a sample and may be used to deplete one or more analyte from a sample.

Advantages of Using Molecular Nets

Molecular and cellular testing strategies employ the use of single-plex or multi-plex immunoassays, PCR assays, next-generation sequencing techniques or other to identify the presence of or to measure the amount of one or more analyte in a sample.

In multiplexed assays, reactions may be separated spatially or may be combined into a single testing reaction and may employ solid phases comprising unique identifiers to provide information. Some examples of unique identifiers may comprise the use of different barcodes, different fluorescence emissions, different chemistries, different ordered nucleotide tags, or other.

Solid phases may be used in single-plex and multi-plex assays may rely on the specific binding of target analyte to produce a measurable signal or a measurable change in signal and may be used in a direct assay or may be used in an indirect assay. Measurable signals may be generated from a positive test and may comprise electric, thermal, magnetic, optical, vibrational, isotopic, or other measurable characteristic.

Many of the difficulties in achieving sensitive and reproducible measurements using current strategies result in high non-specific binding, lower sensitivity, low signal-to-noise and thereby require upstream sample processing steps to remove as many non-specific components from a sample, coupled with the use of highly sensitive reader technologies and complex algorithms which may be required in order to determine real signal from the noise, which make them difficult to translate to truly real-time, easy-to-use molecular diagnostics and analyte measurement tools.

Molecular Nets may be used in place of current commercial approaches and may generate specific and sensitive analyte capture, detection and measurement from a sample. Examples of results obtained from the use of Molecular Nets in place of current approaches for analyte capture are presented in FIGS. 1-6. Improvements in assay sensitivity, minimum levels of analyte detection, and other features may be obtained through the use of a Molecular Net in place of current 2D approaches for analyte capture and measurement. Reduction in background noise may be obtained through the use of a Molecular Net in place of current 2D approaches and may be used to improve analyte purification, analyte purity, and assay sensitivity.

Advantages of a Molecular Net are presented in Table 4 and may include: the rapid capture of one, several or a plurality of molecular and cellular analytes in a raw sample; ability to generate sensitive and specific signals when used in a test involving indirect and direct detection methods; ability to generate a signal having enhanced fluorescent intensity; ability to concentrate bound analyte; ability to spatially separate bound analyte in a manner that reduces stearic hindrance between analytes and/or between detection molecules; enhanced stability; reduced background and others.

TABLE 4

Demonstrated Advantages of Molecular Nets

| Demonstrated Advantages | Anticipated Impact |
|---|---|
| Finger stick by lancet (~50 uL) | Displaces the need for venipuncture |
| No sample prep - compatible with raw, unprocessed sample | Displaces the need for sample processing - both centrifugation & serum isolation (saves time) |
| Point-of-use testing | Displaces the need and cost of sample transport, with ultimate potential for testing at home or in field settings |
| Portability, no complex capital equipment | Displaces the need and cost for off-site CLIA labs |
| Provides immediate answers (<30 mins) | Enables point-of-care treatment and patient monitoring |
| Multiplexing (multi-analyte analysis) | Delivers more robust answer and eliminates the cost of having to run separate tests per sample |
| Simple test procedure | Displaces the need for high-complexity testing (Western blot, Luminex, bead arrays, and PCR) |
| Capable of producing simple actionable readouts (Binary - No/Yes; Semi-quantitative - Low, Mid, High; Fully quantitative) | Enables health care provider (and/or ultimately the patient) to make decision sooner; flexible data output enables numerous applications |
| Stability of test (enzyme-free) = longer shelf life | Increases shelf life, & reduces costs associated with storage issues |
| Cost effective | Disposable cassette with the potential for multiple-tests-in-1 |
| High signal, very low noise (demonstrated femtogram range in multiple test types) | Significantly more sensitive than current immunoassays |

Molecular Nets and their Use

Molecular Nets may be used in applications where analyte binding efficiency, analyte binding kinetics, analyte binding capacity, analyte detection, analyte measurement, analyte enrichment, analyte purification and analyte delivery may be important. Molecular Nets may be used in fluid phase or may be attached to a solid phase.

Molecular Nets may be attached through absorption or covalent processes on a receptive surface. Examples of solid phases include but are not limited to nanotubes, metals, particles, microtiter plates, slides, cassettes, probes, lateral flow tests, stents, catheters, valves, blood tubes, needles, solid phase devices or other. Examples of chemistries of various solid phases that may be compatible for Molecular Net attachment include but are not limited to plastics, other polymer, thin film, colloidal metals, silica, carbon nanotube, protein, carbohydrate, lipid, nucleic acid, cell, tissue or other.

Molecular Nets may be attached to a solid phase device surface to capture, purify or deplete one or more analyte from a sample. An example of using a Molecular Net for analyte capture and/or purification from a sample is presented in FIG. 1. Some other examples of Molecular Nets that may be used to capture and purify analyte from a sample are: Protein A, Protein G or Protein L Net-coated microspheres for immunoglobulin capture; Streptavidin Net-coated microspheres for biotin capture; TNF Net-coated microspheres for anti-TNF biologic capture; IL6 Net-coated microspheres for anti-IL6 biologic capture; IgM Net-coated microspheres for RNA virus capture; Ig Fc Net-coated microspheres for complement capture; antigen Net-coated micro spheres for antigen-specific immunoglobulin; antigen-specific immune cell capture; and others. Molecular Nets may be used in chromatography methods for the capture and purification of one or more analyte from a sample.

Molecular Nets may be used to capture analyte from a sample for downstream analyte measurement by an independent method, referred to herein as sample prep. Examples of independent methods may include mass spectrometry, immunoassay, PCR, next-generation sequencing, qRT-PCR, digital PCR, microscopy, fluorescence, flow cytometry, bead cytometry, or other.

In another aspect, the invention improves signal-to-noise ratios when used in an assay.

Molecular Nets may be attached to a solid phase device surface to measure the presence, absence, modification or concentration of one or more analyte. Examples of using Molecular Nets for analyte detection and/or measurement are presented in FIGS. 3 and 4. In some other examples, Molecular Nets may be used to simultaneous detect and measure 2 or more specific analytes in a direct or indirect manner. Indirect capture by a Molecular Net may relate to the capture of a primary analyte by a specific capture molecule of a Molecular Net that may enable the detection of one or more related secondary associated with the captured primary analyte. Molecular Nets may be used as discovery tools capture primary analytes from a sample and enables the identification, detection or measurement of secondary analytes that are captured-by-association. Molecular Nets may be used in this manner for drug discovery, pathway mapping, and in proteomics, transcriptomics, glycomics, lipidomics, metabolomics, functional genomics, foodomics, nutrition, pharmacology, toxicology and others.

In some examples, Molecular Nets may be used to detect drug resistance in a cell. Cells may be tumor cells, immune cells, microbial cells or other cells. Molecular Nets for these applications may comprise capture molecules directed against one or more unique features of a cell type. Molecular Nets may additionally be fabricated in a manner to impart surface topology relating to the capture of in tact cells.

In other examples, Molecular Nets may be fabricated and used in: immune cell reactivity measurement; immune response monitoring; immune response classification; immunoglobulin titering; biotinylated molecule capture;

multiplex immunoassays; singleplex immunoassays; next-generation sequencing reactions; PCR; microbiome capture; microbiome discovery; mRNA and encoded protein measurement; SNP (single nucleotide polymorphisms) mapping; SNP detection; disease marker sample preparation; miRNA capture and/or measurement; post-translation modification discovery and/or capture and/or measurement; kinase activity measurement; or other.

Molecular Nets may have measurable characteristics imparted during the fabrication process and may be used in a direct or indirect manner as a sensor. A measurable change in one or more characteristic of a Molecular Net sensor may be detected using commercial approaches employing the use of optical sensing, electrochemical sensing, electromagnetic sensing, electrical impedance, or other. In one example, a Molecular Net sensor may be used to capture and bind an analyte. Analyte binding may result in a measurable change in a characteristic of a Molecular Net sensor. A binding event or modifying event pertaining to the Molecular Net sensor may be monitored over a period of time, and the changes in Molecular Net sensor characteristics may be detected, relayed and collected by a device. Other examples of using a Molecular Net as a sensor may include an analyte binding event, enzymatic reaction, analyte modification event, cell differentiation, cell-cell interaction, or other.

Examples of measurable characteristics include but are not limited to: physical shape, height, density, fluorescence intensity, wavelength shift (FRET or FRAP), vibrational frequency, absorbance, flexibility, refractiveness, conductance, impedance, resistance, melting temperature, denaturation temperature, freezing temperature, and other.

Measuring devices that may be compatible for use with a Molecular Net sensor may comprise: photonic multichannel analyzers, spectrometers, magnetic resonance imagers, magnetic field detectors, optical fibers, glass pipettes, circuits, fluorometers, spectroscopic analyzers, flow cytometers, CCD cameras, microscopes, acoustic chambers, microphones, luminometers, and other. The measuring devices may be used to measure changes in: thickness, topology, charge, insulation, capacitance, voltage, color, acoustics, vibration, magnetism, enzymatic activity or other characteristics of a Molecular Net used as a sensor.

Additionally, Molecular Nets may be used in flexible circuits, whereby the capture molecules and/or structural molecules may be connected to conductive molecules. Molecular Net circuits may be used in single-sided flexible circuits, double access (back bared flex circuits), sculptured flex circuits, double-sided flex circuits, multilayered flex circuits, ridge flex circuits, ridge-flex boards, polymer thick film flex circuits or other. Most flexible circuits are passive wiring structures that are used to interconnect electronic components such as integrated circuits, resistor, capacitors and the like, however some are used only for making interconnections between other electronic assemblies either directly or by means of connectors. Molecular Nets for use in circuits or for use as a component of a circuit may be comprised of synthetic components or may be comprised of biochemical capture molecules and/or cells and may be fabricated in a manner to be used in a flexible circuit. Molecular Net circuits may also be used as a sensor.

In some examples, Molecular Net circuits may have specific electrochemical properties and may be used to monitor various parameters such as pH, current, voltage, impedance, or other in an electrochemical/electrolyte cell. Binding events and modifying events that may occur to Molecular Net may be measurable and may be reflected by a change in the conductance, current, or voltage. More specifically, the introduction of a sample containing an analyte that has specific binding affinity for, or is reactive towards, a component in a Molecular Net circuit may be monitored by a change in the electrochemical properties of the Molecular Net and/or the surrounding environment.

Examples of binding events on a Molecular Net used in a circuit may include: antibody-antigen interaction, nucleic acid-nucleic acid interaction, enzyme-substrate interaction, drug-target interaction, enzyme-co-factor interaction, ligand-cell interaction, or any other specific surface-chemistry-driven non-covalent interaction. Analyte capture by a Molecular Net may be determined by a change in pH, current or voltage an electrochemical/electrolyte cell. Measurement of a change in Molecular Net characteristics may also result from one or more, or an accumulation of modifying events to one or more component in a Molecular Net or to a capture analyte. Examples of modifying events may include: enzyme cleavage; post-translational modification (such as phosphorylation, sulfonation, glycosylation, methylation, or other); removal of a post-translational modification (such as de-phosphorylation); or other similar modification. Modifying events may be determined by a change in pH, current or voltage in the electrochemical/electrolyte cell resulting from a change in Molecular Net characteristics or in the surrounding buffer system.

Methods to determine changes in electrochemical properties of a Molecular Net used in a circuit may include the use of scanning ion current microscopy, nanofluidic diodes, nanopores or nanochannels that display voltage-gated ion current, ion nanogating, nanopore-based sensing platforms and other methods for measuring the flow, or changes in flow of electrical charge through a medium. More specifically, the inherent sensitivity of many solid-state nanopore sensors is the selective permeability of electrolytes, or ion current, when a bias is applied across the nanopore. Molecular Nets may be coated onto the surface of a nanopore and the change in current, voltage, and impedance can be monitored.

Molecular Net can also be coated onto the surface of a carbon nanotube and whereby the molecular Net can be constructed in a manner to generate size exclusion and affinity requirements for analyte sensing.

Bio-Layer Interferometry (BLI) is a label-free technology for measuring biomolecular interactions. It is an optical analytical technique that analyzes the interference pattern of white light reflected from two surfaces: a layer of immobilized molecular Net on the biosensor tip, and an internal reference layer. Any change in the number of molecules bound to the biosensor tip causes a shift in the interference pattern that can be measured in real-time. The binding between a ligand immobilized on the molecular Net-coated biosensor tip and an analyte in solution produces an increase in optical thickness at the biosensor tip, which results in a wavelength shift, $\Delta\lambda$, which is a direct measure of the change in thickness of the biological layer. Interactions may be measured in real time, providing the ability to monitor binding specificity, rates of association and dissociation, or concentration, with precision and accuracy. Only molecules binding to or dissociating from the Molecular Net biosensor may shift the interference pattern and generate a response profile. Unbound molecules, may change the refractive index of the surrounding medium, or may change flow rate but will not affect the interference pattern. This is a unique characteristic of BLI and extends its capability to perform in crude samples used in applications for analyte—capture molecule binding, quantitation, affinity, and kinetics.

Molecular Net particles may also be used to deliver an active agent. Active agents may be pre-loaded onto capture molecules located in one or more layer of a Molecular Net. Active agents may comprise: drugs, therapeutics, toxins, viruses, allergens, vaccine components, antigens, immune modulators, surfactants, microbes, oligonucleotides, nutrients, or other. Molecular Net particles may be used in drug or therapeutic delivery, vaccine delivery, in biofermentation or other. Molecular Nets may comprise one or more targeting agent on a surface-exposed layer to facilitate specificity in targeting said Molecular Net particle to a specific cell type, tissue type, organ type or other. Targeting agents may be capture molecules of a Molecular Net. Targeting agents may comprise: antibodies, receptors, ligands, anti-ligands, or other. Targeting agents in a Molecular Net may be covalently linked to capture molecules, linkers, and spacers in a surface-exposed layer. Targeting agents may also contribute to the topological features of a Molecular Net.

EXAMPLES

Example 1. Comparison of Conventional 2D and 3D Molecular Net Microparticles for Analyte Purification Molecular Nets comprised of monomeric protein G and linked protein G and crosslinkers $BS^3$, EMCS, EGS, BMPH and others were used in fabrication. Molecular Net fabrication occurred in real-time on 0.8-10 um magnetic polystyrene microparticle and 45 um nitrocellulose microparticle surfaces. In some examples, the capture molecule, protein G was used as the only source of structural support. In some examples, pre-linked protein G and monomeric protein G were mixed to serve as additional structural support for fabrication of some layers of the Molecular Net. Yet in some other examples, a first layer of Molecular Net comprised protein G and Ig Fc region to serve as structural support for fabrication of additional layers of the Molecular Net. In some examples, a protein G Molecular Net comprised 2 layers and in other examples, a protein G Molecular Net comprised 3 layers. The last layer of the Molecular Net comprised topological features to enhance analyte (in this case IgG) binding and recovery from a sample. FIG. 1 is an example of data obtained using protein G Molecular Net microparticles in comparison to commercial protein G microparticles. Briefly, IgG-Alexa 647 was spiked into human serum (1 ug/tube). Uncoated microparticles, commercial protein G microparticles and protein G Molecular Net microparticles were incubated with spiked sample for 15-60 min at RT (at 100,000 particles (uncoated control), 100,000 particles (commercial) and 25,000 particles (Molecular Net). Particles were isolated from samples using magnetic separation and were washed 3× in PBST. Particles were resuspended in 2×LSB, boiled and loaded onto an SDS-PAGE. Recovered IgG was measured by Coomassie-stained band densitometry compared to input control. Depicted in FIG. 1 is the percent recovery of input for each purification type. Use of an optimized Molecular Net can reduce background noise in an assay and increase a visible signal.

Figure 2:
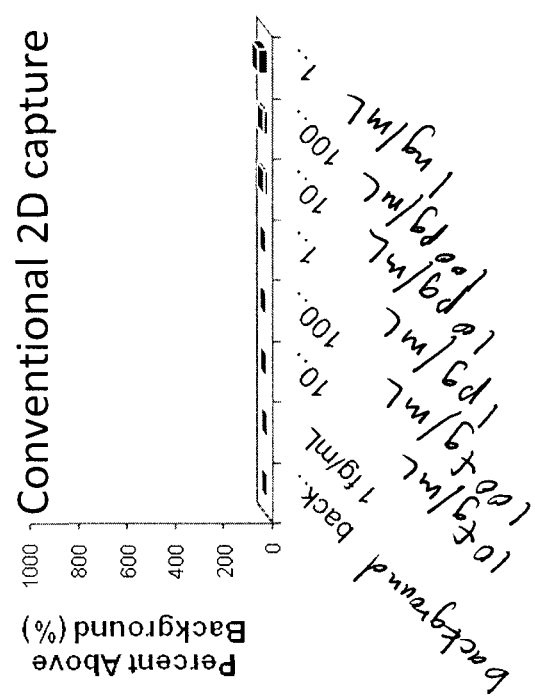
FIG. 2 shows a traditional capture molecule conjugation to microparticles and the corresponding analyte measurement capability.

Example 2. Effectiveness of Conventional 2D Conjugates for Analyte Detection Traditional approaches to covalently link capture antibody to a surface is a 2-dimensional approach (X and Y planes). as there are no additional layers added onto the surface of the linked antibodies on a surface. Traditional methods used to covalently link capture antibody to a surface involve a single type of linker, for example EDC, NHS, sulfo-NHS or other. Occasionally, a second linker is used to secure the capture antibody to a surface, but involves removal of the first linker and does not add additional height or layering to the antibody-conjugated surface. In an example, per manufacturer instructions, anti-human neuroserpin antibody was coupled to Luminex particles (bead region #54) by linker. Particles were then quenched, blocked, and washed prior to use. Particles were incubated for 15 min in pre-cleared serum+neuroserpin at a concentration range of (0-1 ng/mL). Bound particles were washed and incubated with biotin-anti-Neuroserpin (10 ng/mL) for 15 min. Neuroserpin detection was visualized by avidin-PE (30 ng/mL) for 15 min. Washed particles were then analyzed on a Luminex 100, collecting 100 particles per sample. Presented in FIG. 2 is the median fluorescence intensity (FI) at each dilution above background fluorescence intensity.

Figure 3:
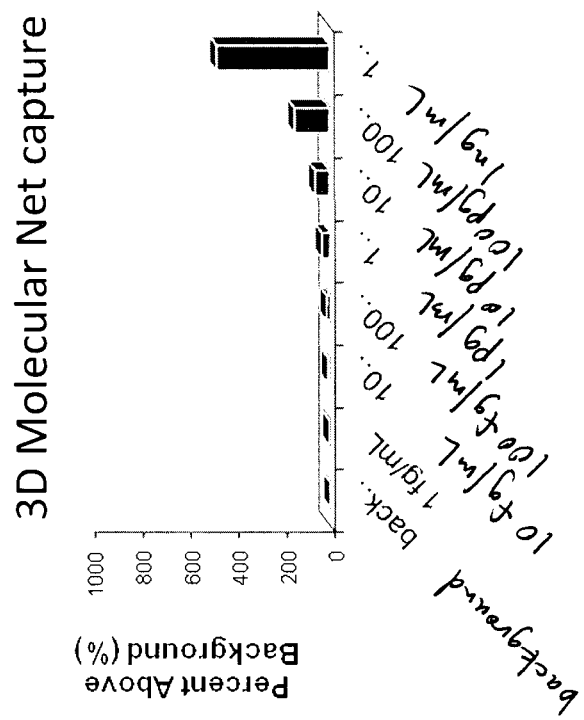
FIG. 3 shows an effectiveness of Molecular Net microparticles in measuring analyte.

FIG. 3. Effectiveness of Molecular Net Microparticles in Measuring Analyte

Molecular Net comprised of identical anti-human neuroserpin antibody (as FIG. 2) and linkers Sulfo-NHS, EMCS, EGS, BMPH and others was fabricated to provide a 3-dimensional multi-layered (X, Y, and Z planes) matrix. The Molecular Nets were then covalently linked to Luminex microparticles (bead region #54). Assay performance with the 4-layered Molecular Nets are presented in FIG. 3. Improved assay MFI was observed using a 3-dimensional multi-layered Molecular Net.

Figure 4:
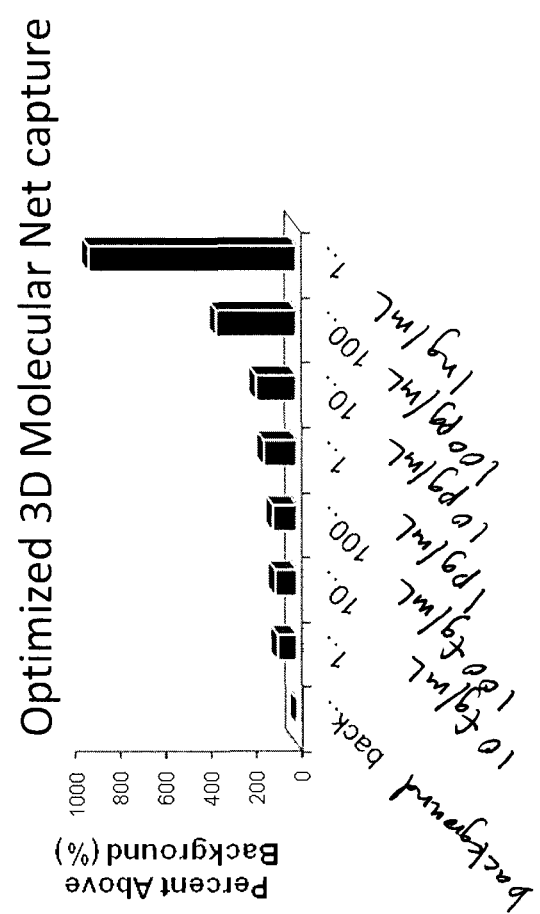
FIG. 4 shows an effectiveness of a Molecular Net with topology in measuring analyte.

FIG. 4. Effectiveness of a Molecular Net with Topology in Measuring Analyte

Molecular Net comprised of identical anti-human neuroserpin antibody (as FIGS. 2 and 3) and linkers Sulfo-NHS, EMCS, EGS, BMPH and others was fabricated to provide a 3-dimensional multi-layered (X, Y, and Z planes) matrix. The Molecular Nets were then covalently linked to Luminex microparticles (bead region #54). Assay performance with the 5-layered Molecular Nets are presented in FIG. 4. Improved assay MFI was observed using a 3-dimensional multi-layered Molecular Net with enhanced topology in the outer layers.

Figure 5:
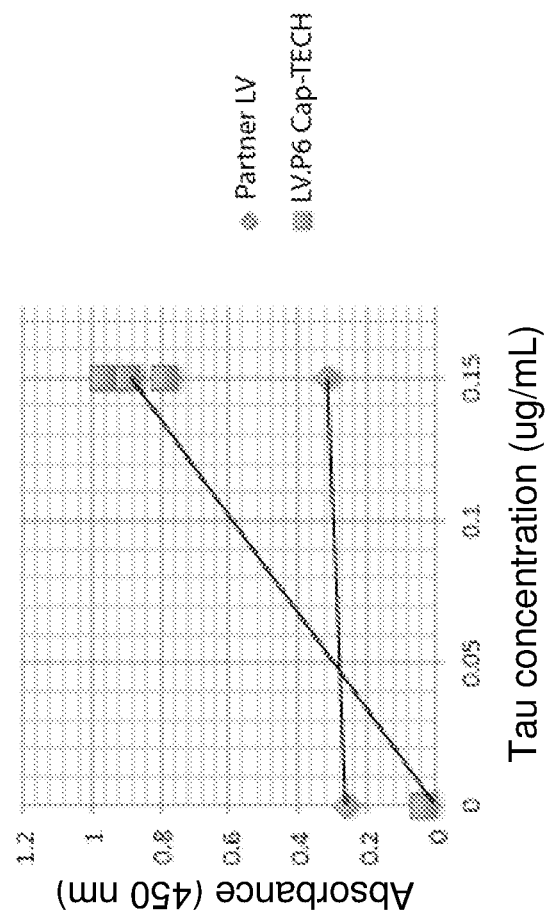
FIG. 5 shows a comparison of traditionally conjugated microparticles and Molecular Net microparticles in a Tau ELISA.

FIG. 5. Comparison of Traditionally Conjugated Microparticles and Molecular Net Microparticles in an ELISA Molecular Nets comprised of monoclonal antibody directed against human-TauF and crosslinkers Sulfo-NHS, EMCS, EGS, BMPH and others were used in fabrication. Molecular Net fabrication occurred in real-time on 0.5, 6.3 and 10 um magnetic microparticle surfaces. In some examples, the capture molecule, anti-Tau mAb, was used as the only source of structural support. In some examples, the spacer, albumin, was mixed with the anti-Tau mAb in a first layer at a 1.5:1.0 Molar ratio (albumin:anti-Tau Ab) to serve as additional structural support for fabrication of the first layer. In some examples, a second capture molecule, human tubulin was used and provided both structural support and capture roles within a Molecular Net. FIG. 5 is an example of data obtained using an anti-Tau Molecular Net (LV.P6 Cap-TECH) in comparison to a commercial Tau microparticle (Partner LV) ELISA (identical assay conditions, identical antibody pair, etc.). FIG. 5 is an example of using a Molecular Net to reduce background noise in an assay and increase a visible signal in an ELISA.

Figure 6:
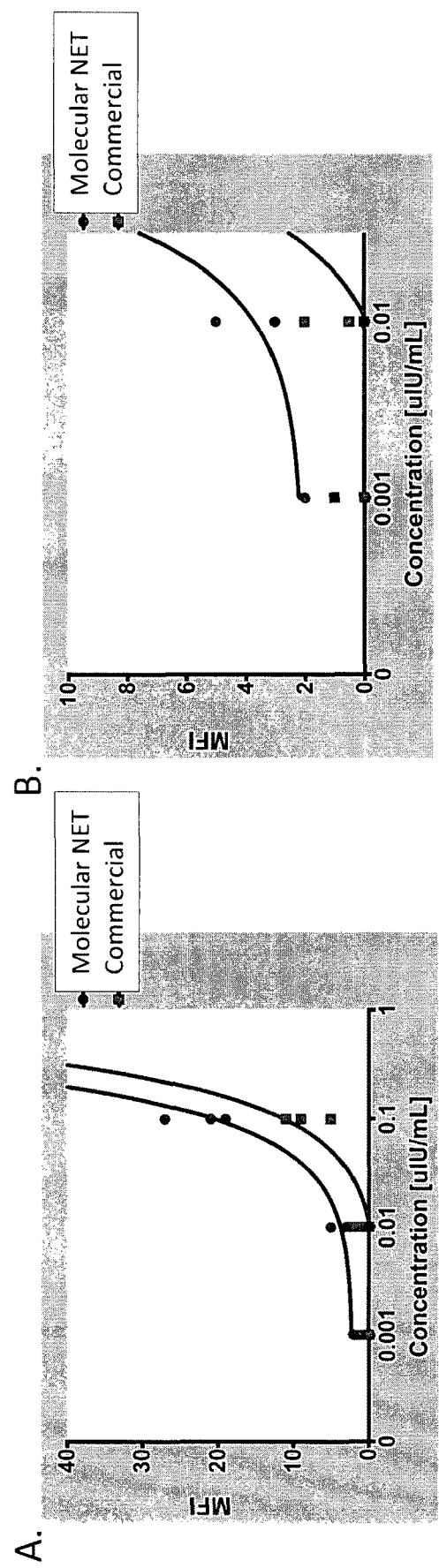
FIG. 6 shows a comparison of traditionally conjugated microparticles and Molecular Net microparticles in a TSH Luminex sandwich immunoassay.

FIG. 6. Comparison of Traditionally Conjugated Microparticles and Molecular Net Microparticles Using Luminex Molecular Net comprised of monoclonal antibody directed against human-thyroid stimulating hormone and crosslinkers EDC, BS(PEG)$_9$, EMCS, EGS, BMPH and others were used in fabrication. Molecular Net fabrication occurred in real-time on Luminex magnetic microparticle surfaces. In some examples, the capture molecule, anti-TSH mAb, was used as the only source of structural support. In some examples, the spacers, PEG, heat-denatured lysozyme and others were mixed with the anti-TSH mAb in a first layer at a 1.0:2.0 Molar ratio (spacer:anti-TSH Ab) to serve as additional structural support for fabrication of the first layer. In some examples, an anti-TSH Molecular Net comprised 4 layers and in other examples, an anti-TSH Molecular Net comprised 6 layers with the last layer comprising topological features to enhance analyte binding and performance in a Luminex. FIG. 6A is an example of using a Molecular Net to increase the overall MFI in a Luminex assay. FIG. 6B is exemplary data obtained in a Luminex assay to increase the minimum levels of detection in a Luminex assay.

Figure 7:
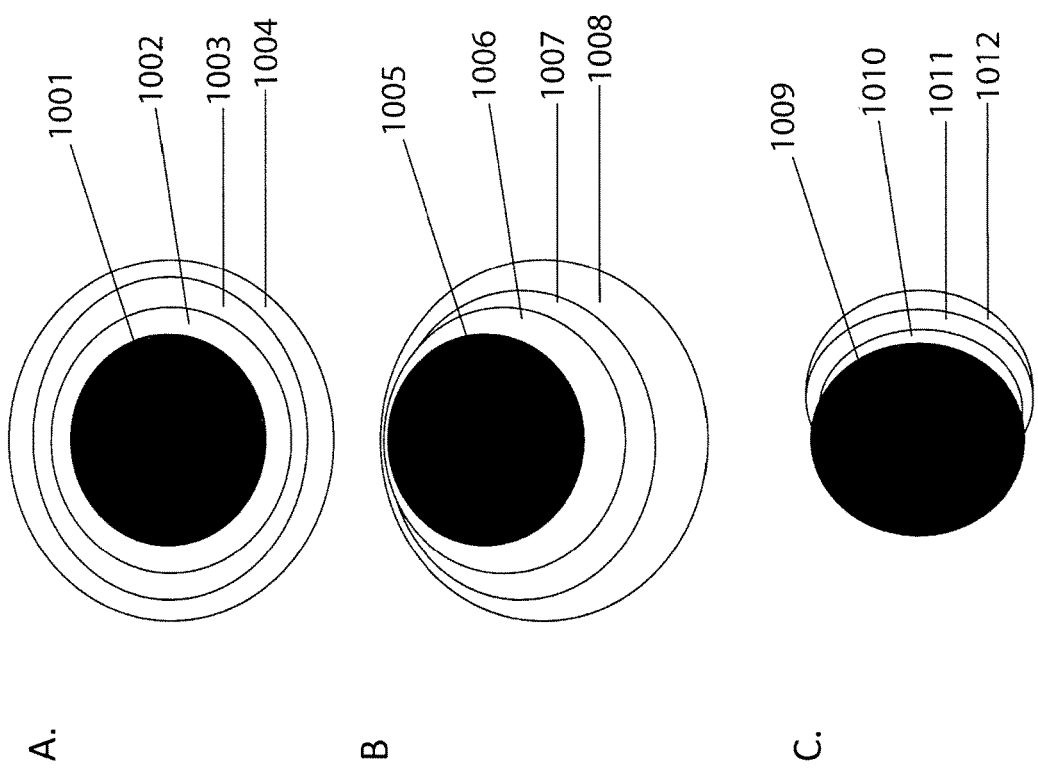
FIG. 7 shows an exemplary Molecular Nets on particles.

FIG. 7. Exemplary Molecular Nets on Particles

FIG. 7 depicts some examples in which Molecular Nets may be placed onto a particle surface. In some examples, a Molecular Net is placed on a particle surface (FIG. 7A, 1001) in a circumferential manner whereby a Molecular Net having X, Y and Z spatial orientation may be fairly symmetrical and where each layer (examples of 3 layers, 1002, 1003 and 1004) adds to the Z plane of the particle. In some examples, Molecular Nets may be placed onto a particle surface (FIG. 7B, 1005) in an asymmetrical manner whereby a Molecular Net having X, Y and Z spatial orientation may be placed onto the surface of a particle in a manner to generate a polarity of the particle and where each layer (examples of 3 layers, 1006, 1007 and 1008) adds to the Z plane of the particle in a layer-dependent manner (for example, some layers may have less height and other layers may have more height). In other examples, Molecular Nets may be placed onto a portion of particle surface (FIG. 7C, 1009) in an asymmetrical manner whereby a Molecular Net having X, Y and Z spatial orientation may be placed onto the surface of a particle in a manner to generate a polarity of the particle and where each layer (examples of 3 layers, 1010, 1011 and 1012) adds to the Z plane of the particle in a layer-dependent manner (for example, some layers may have specificity for an analyte and other layers may have specificity for other analytes).

Figure 8:
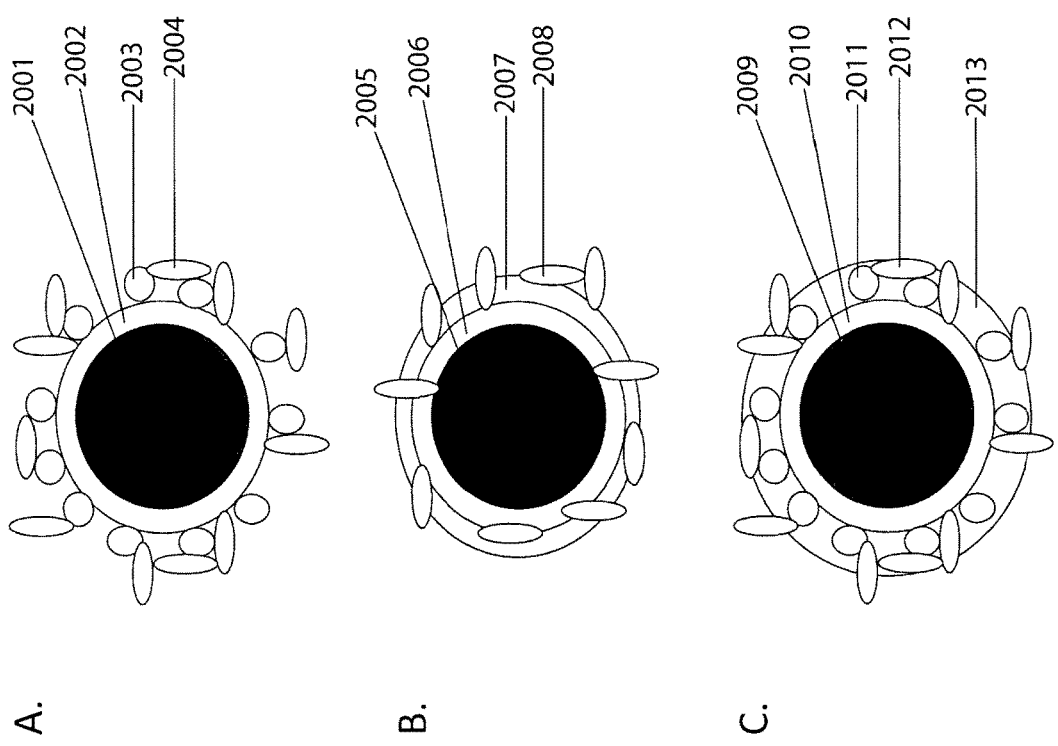
FIG. 8 shows an exemplary Molecular Net topological features on particles.

FIG. 8. Exemplary Molecular Net Topological Features on Particles

FIG. 8 depicts some examples in which Molecular Nets may be placed onto a particle surface. In some examples, a Molecular Net is placed on a particle surface (FIG. 8A, 2001) in a circumferential manner whereby a Molecular Net having X, Y and Z spatial orientation may be fairly symmetrical in one layer (2002) and where each layer (examples of 3 layers, 2002, 2003 and 2004) adds to the Z plane of the particle in differing and asymmetric ways (for example, topology is generated). In some examples, Molecular Nets may be placed onto a particle surface (FIG. 8B, 2005) in an asymmetrical manner whereby a Molecular Net having X, Y and Z spatial orientation may be placed onto the surface of a particle in a manner to generate structural features (2008) throughout layers 1 (2006), 2 (2007) and 3 (2008) of the particle and where each layer adds to the Z plane of the particle in a layer-dependent manner (for example, some layers may have less height and other layers may have more height). Additionally, the structural elements in each layer may also serve an analyte capture role in a Molecular Net. In other examples, Molecular Nets may be placed onto a portion of particle surface (FIG. 8C, 1009) in an asymmetrical manner whereby a Molecular Net having X, Y and Z spatial orientation may be placed onto the surface of a particle in a manner to generate a polarity of the particle and where each layer (examples of 4 layers, 2010, 2011, 2012 and 2013) adds to the Z plane of the particle in a layer-dependent manner and whereby each layer may serve both structural and analyte capture roles. For example, some layers may have specificity for an analyte based on size (e.g., FIG. 8C, 2010) and outer layers (e.g., FIG. 8C, 2013) may have specificity for analyte of a larger size.

Figure 9:
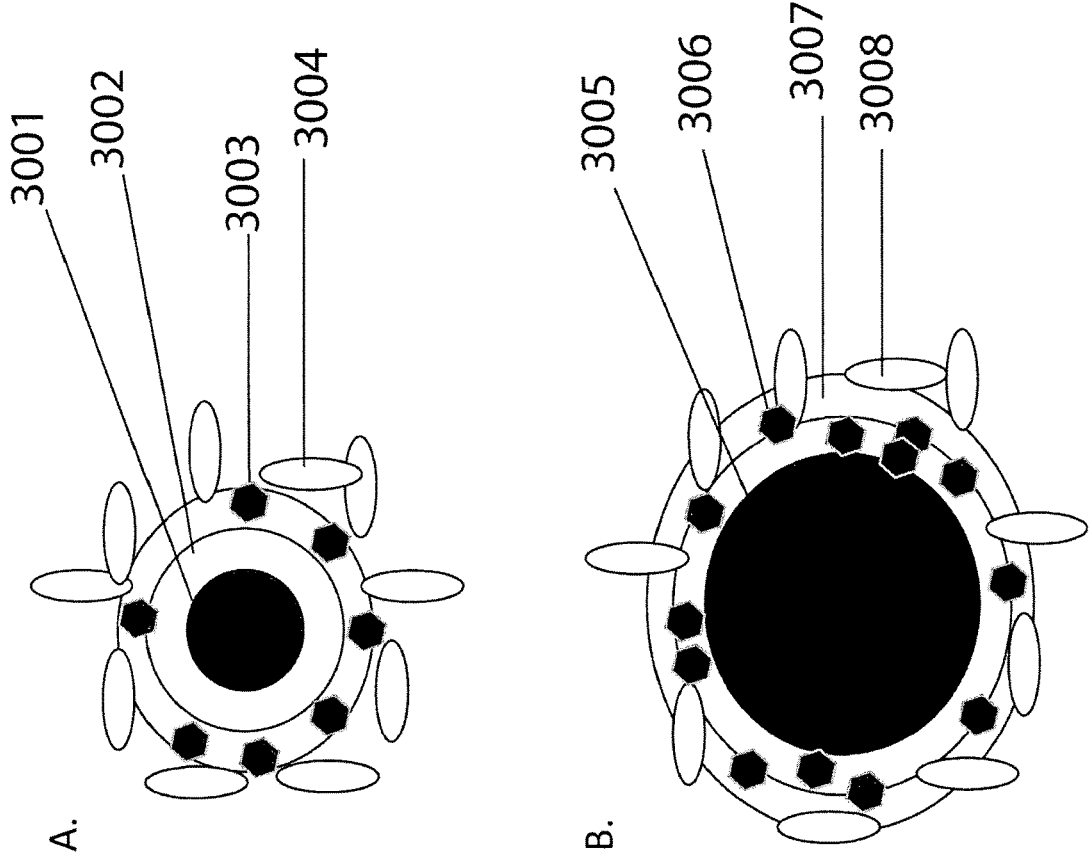
FIG. 9 shows an exemplary Molecular Nets for analyte delivery.

FIG. 9. Exemplary Molecular Nets for Analyte Delivery

FIG. 9 depicts some examples in which Molecular Nets may be placed onto a particle surface for use in analyte capture or targeted analyte delivery. In some examples, a Molecular Net is placed on a particle surface (FIG. 9A, 3001) in a circumferential manner whereby a Molecular Net having X, Y and Z spatial orientation may be fairly symmetrical in one layer (3002) and where each layer (examples of 3 layers, 3002, 3003 and 3004) adds to the Z plane of the particle in differing and asymmetric ways (for example, topology is generated). In some examples, analyte cargo (3003) may be pre-loaded onto capture molecules in one or more layer of a Molecular Net. In outer layers, different capture molecules may be linked into a Molecular Net to generate a topology and/or an affinity for a different target analyte. In some examples, a pre-loaded analyte may comprise a drug, a therapeutic, siRNA, miRNA, dsRNA, virus, toxin, immunogen or other. Pre-loaded cargo may be non-covalently associated with one or more type of capture molecule in a layer of a Molecular Net. In some examples, different capture molecules (3004) of a Molecular Net may be arranged in the outer layers of a Molecular Net and may serve topological and analyte capture roles. The different capture molecules may have specificity for one or more different analyte, the analyte of which may comprise an antibody, an anti-ligand, a ligand, a receptor, an antigen or other and may serve one or more structural and/or affinity and/or targeting role.

In some examples, Molecular Nets may be placed onto a particle surface (FIG. 9B, 3005) in a manner whereby analyte cargo (3006) may be pre-loaded in all layers of a Molecular Net. In some layers, capture molecules may be used to generate topological features (3008) that serve particle-targeting roles. In some examples, outer layers of a Molecular Net particle may target said particle to a specific cell, tissue, organ or other.

Figure 10:
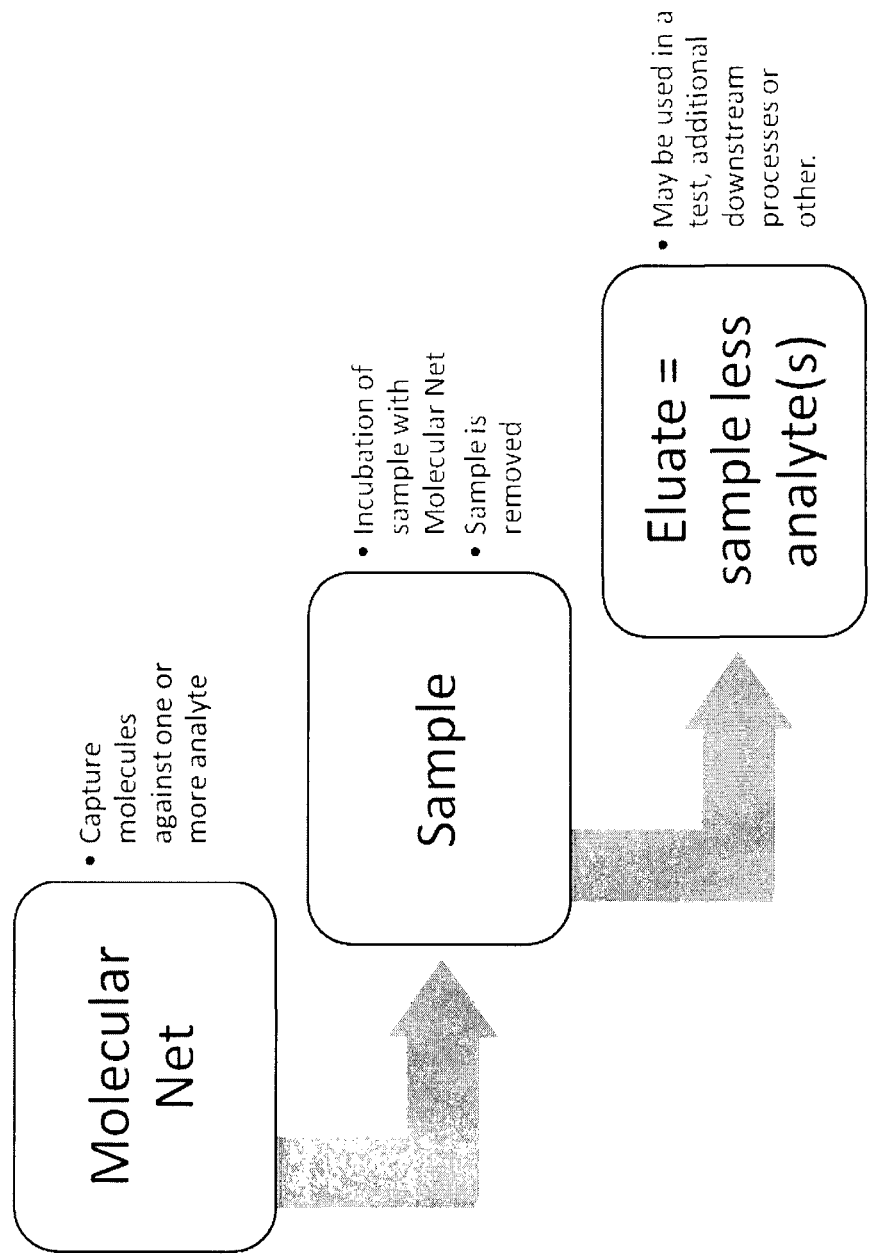
FIG. 10 shows examples of Molecular Nets for analyte purification from a sample.

FIG. 10. Molecular Nets for Analyte Purification from a Sample

Molecular Nets may be used in sample purification processes (example is provided in FIG. 10). In some examples, Molecular Net designed and fabricated to deplete one or more analyte may be used to treat a sample for analyte depletion. Exemplary methods may include incubation of Molecular Net with sample for about 15 minutes to about 24 hours in a batch slurry or in a chromatography column. Sample supernatant or flowthrough may be collected depending on preferred method. Molecular Nets may be collected and analyzed using various methods for the presence and amount of captured analyte. Molecular Net-treated sample may be collected and analyzed using various methods to determine the residual presence of analyte in the sample or may be analyzed for other analytes in the sample.

Figure 11:
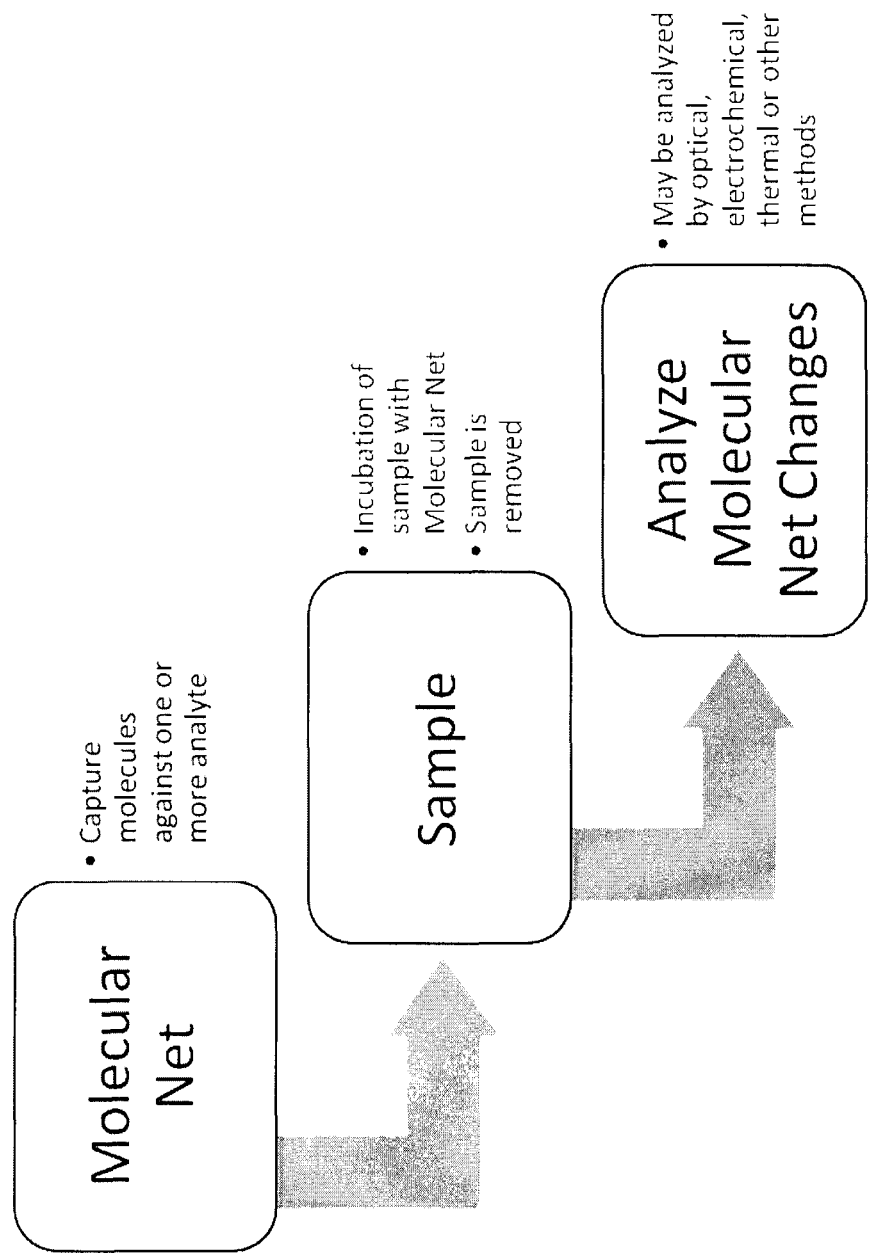
FIG. 11 shows examples of Molecular Nets for analyte detection and measurement from a sample.

FIG. 11. Molecular Nets for Analyte Detection & Measurement from a Sample

Molecular Nets may be used in an analyte measurement tool or a diagnostic tool (example is provided in FIG. 11). In some examples, Molecular Net designed and fabricated to capture one or more analyte may be used to treat a sample for analyte detection and measurement. Exemplary methods may include incubation of Molecular Net with sample for about 15 minutes to about 2 hours in a batch slurry, cassette, slide, microtiter plate or other. Sample supernatant or flowthrough may be collected depending on preferred method. Molecular Nets may be collected and analyzed using various methods for the presence and amount of captured analyte(s). Molecular Net-treated sample may also be collected and analyzed using various methods to measure other analytes. Methods for measuring changes in Molecular Net characteristics may include optical, electrophoretic, electrical, magnetic, chemical, thermal or other.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modification are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

What is claimed is:

1. A composition comprising:
   (a) a solid phase;
   (b) a molecular net capable of binding to at least one analyte and coupled to at least a portion of a surface of the solid phase, the molecular net comprising more than one layer, which more than one layers comprise at least a first layer and a second layer, and each of the layers comprises capture molecules capable of specifically binding to the analyte(s); and,
   (c) at least two different linker molecules,
   wherein:
      the capture molecules are coupled to each other within each layer by the at least two different linker molecules,
      the molecular net is an internally covalently-linked three dimensional matrix,
      the capture molecules within each layer can be of the same or different types,
      the capture molecules of one layer can be of the same or different types as the capture molecules of another layer,
      one of the at least one analyte is an exosome, and
      the capture molecules comprise more than one antibodies directed to exosomes.

2. The composition of claim 1, wherein the molecular net comprises three, four, five, or six layers.

3. The composition of claim 1, wherein the capture molecules of each layer are different.

4. The composition of claim 1, wherein the layers have different porosities from each other.

5. The composition of claim 1, wherein each layer comprises at least one topological feature which affects the porosity of the layer.

6. The composition of claim 5, wherein the at least one topological feature comprises one or more of fissures, channels, pores, or pockets.

7. The composition of claim 1, wherein the last constructed layer has a porosity that is greater than porosity of any other layer.

8. The composition of claim 1, wherein the porosity increases from the first constructed layer to the last constructed layer.

9. The composition of claim 1, wherein at least one of the more than one antibodies is a monoclonal antibody.

10. The composition of claim 1, wherein the more than one antibodies are directed to (a) one or more exosome proteins, (b) one or more exosome lipids, (c) one or more exosome carbohydrates, or (d) combinations thereof.

11. The composition of claim 1, wherein the more than one antibodies are directed to one or more exosome proteins.

12. The composition of claim 1, wherein the capture molecules further comprise one or more of nucleic acid probes, enzymes, recombinant proteins, or peptides.

13. The composition of claim 1, wherein the capture molecules of the first layer, the capture molecules of the second layer, or both, are also coupled to each other by a plurality of different types of spacer molecules.

14. The composition of claim 13, wherein the spacer molecules comprise one or more of PEGs, polymers, nucleic acids, albumins, Fe regions, or peptides.

15. The composition of claim 14, wherein at least one of the plurality of different types of spacer molecules give the molecular net at least one pore having a diameter of between 40 and 500 nm.

16. The composition of claim 1, wherein each layer comprises at least one topological feature that affects the porosity of the layer, wherein the topological feature is a pore having a diameter of between 40 and 500 nm.

17. A device for capturing at least one analyte comprising
   (1) a solid phase and
   (2) a capture composition having a molecular net capable of binding to the at least one analyte and coupled to at least a portion of a surface of the solid phase, the capture composition comprising more than one layer, which more than one layers comprise at least a first layer and a second layer, and each of the layers comprises capture molecules capable of specifically binding to the analyte(s); and,
   (c) at least two different linker molecules,
   wherein:
      the capture molecules are coupled to each other within each layer by the at least two different linker molecules, the molecular net is an internally covalently-linked three dimensional matrix, the capture molecules within each layer can be of the same or different types, the capture molecules of one layer can be of the same or different types as the capture molecules of another layer, one of the at least one analyte is an exosome, and the capture molecules comprise more than one antibodies directed to exosomes.

18. The device of claim 17, wherein the solid phase is made of one or more of a plastic, polymer, thin film, colloidal metal, silica, carbon nanotube, protein, carbohydrate, lipid, nucleic acid, cell, or tissue.

19. The device of claim 17, wherein the solid phase comprises one or more of a nanomaterial, modified metal surface, nanosphere, microsphere, microtiter plate, slide, pipette, cassette, cartridge, disc, probe, lateral flow device, microfluidics device, or optical fiber.

20. The device of claim 17, wherein the capture composition is prefabricated and absorbed to the surface of the solid phase.

21. The device of claim 17, wherein the capture composition is covalently linked to the surface of the solid phase.

22. The device of claim 17, wherein the capture composition is constructed directly on the surface of the solid phase.

23. The device of claim 17, wherein the capture composition comprises more than one layer and the linker molecules of the first layer, the linker molecules of the second layer, or both, comprise one or more of homobifunctional, heterobifunctional, trifunctional, or multifunctional types.

24. The device of claim 17, wherein the capture composition comprises more than one layer and the capture composition has at least one measurable characteristic that undergoes a change when the capture molecules of the first layer, the capture molecules of the second layer, or both, bind to at least one analyte.

25. The device of claim 24, wherein the measurable characteristic comprises one or more of physical shape, height, density, fluorescence intensity, wavelength shift, vibrational frequency, absorbance, flexibility, refractiveness, conductance, impedance, resistance, melting temperature, denaturation temperature, or freezing temperature.

26. The device of claim 17, wherein the solid phase comprises an underlayer and the capture composition is coupled to at least a portion of the underlayer.

27. The device of claim 26, wherein the underlayer does not comprise capture molecules.

28. The device of claim 26, wherein the underlayer does comprise capture molecules and the underlayer capture molecules are capable of binding to at least one analyte.

29. The device of claim 17, wherein the capture composition comprises more than one layer and the first layer is closer to the solid phase than the second layer, and the first layer has a first porosity that is less than a second porosity of the second layer.

30. A method of measuring a quantity of at least one analyte in a sample, the method comprising:

exposing one or more devices of claim 17 to the sample; and allowing at least some of at least one analyte to bind to the capture molecules of the capture compositions of one or more devices.

31. The method of claim 30, wherein the capture composition comprises more than one layer.

32. The method of claim 30, further comprising measuring a change in the sample.

33. The method of claim 32, wherein measuring the change comprises using one or more of a photonic multi-channel analyzer, spectrometer, magnetic resonance imager, magnetic field detector, optical fiber, glass pipette, circuit, fluorometer, spectroscopic analyzer, potentiostat, calorimeter, electrophoresis, flow cytometer, CCD camera, microscope, acoustic chamber, microphone, and luminometer.

34. The method of claim 30, wherein the capture composition has at least one measurable characteristic that undergoes a change when the capture molecules bind to the analyte.

35. The method of claim 30, further comprising measuring the change in the measurable characteristic of one or more capture compositions.

36. The method of claim 35, wherein measuring the change comprises using one or more of a photonic multi-channel analyzer, spectrometer, magnetic resonance imager, magnetic field detector, optical fiber, glass pipette, circuit, fluorometer, spectroscopic analyzer, potentiostat, calorimeter, electrophoresis, flow cytometer, CCD camera, microscope, acoustic chamber, microphone, and luminometer.

37. A method of manufacturing a device for capturing at least one analyte, the method comprising:

placing a capture composition having a molecular net on at least a portion of a surface of a solid phase, the capture composition capable of binding to the at least one analyte and coupled to at least a portion of a surface of the solid phase, the capture composition comprising more than one layer, which more than one layers comprise at least a first layer and a second layer, and each of the layers comprises capture molecules capable of specifically binding to the analyte(s); and, (c) at least two different linker molecules, wherein:

the capture molecules are coupled to each other within each layer by the at least two different linker molecules, the molecular net is an internally covalently-linked three dimensional matrix, the capture molecules within each layer can be of the same or different types, the capture molecules of one layer can be of the same or different types as the capture molecules of another layer, one of the at least one analyte is an exosome, and the capture molecules comprise more than one antibodies directed to exosomes.

38. The method of claim 37, wherein the capture composition comprises more than one layer.

39. The method of claim 37, wherein the placing a capture composition comprises prefabricating the capture composition and absorbing the capture composition to the surface of the solid phase.

40. The method of claim 37, wherein the placing a capture composition comprises covalently linking the capture composition to the surface of the solid phase.

41. The method of claim 37, wherein the placing a capture composition includes constructing the capture composition directly on the surface of the solid phase.

* * * * *